US011740128B2

(12) United States Patent
Katz

(10) Patent No.: US 11,740,128 B2
(45) Date of Patent: Aug. 29, 2023

(54) SYSTEM AND METHOD FOR NON-INVASIVE MEASUREMENT OF ANALYTES IN VIVO

(71) Applicant: Sanguis Corporation, Selden, NY (US)

(72) Inventor: Jeffrey Owen Katz, Selden, NY (US)

(73) Assignee: SANGUIS CORPORATION, Selden, NY (US)

(*) Notice: Subject to any disclaimer, the term of this patent is extended or adjusted under 35 U.S.C. 154(b) by 380 days.

(21) Appl. No.: 16/927,804

(22) Filed: Jul. 13, 2020

(65) Prior Publication Data
US 2021/0025758 A1 Jan. 28, 2021

Related U.S. Application Data

(60) Provisional application No. 62/878,074, filed on Jul. 24, 2019.

(51) Int. Cl.
G01J 3/02 (2006.01)
G01J 3/44 (2006.01)
(Continued)

(52) U.S. Cl.
CPC .............. *G01J 3/4412* (2013.01); *G01J 3/021* (2013.01); *G01J 3/0202* (2013.01);
(Continued)

(58) Field of Classification Search
CPC ........ G01J 3/44; G01J 3/02; G01J 3/06; G01J 2003/062; G01J 2003/064; G01J 3/14;
(Continued)

(56) References Cited

U.S. PATENT DOCUMENTS 5,612,967 A * 3/1997 Lai ........................... G02F 1/37
372/98
5,712,470 A * 1/1998 Katz .................. G06K 7/10574
235/462.32

(Continued)

OTHER PUBLICATIONS

International Search Report and Written Opinion issued in PCT/US20/43189, dated Dec. 21, 2020.

(Continued)

*Primary Examiner* — Abdullahi Nur
(74) *Attorney, Agent, or Firm* — Leason Ellis LLP

(57) ABSTRACT

A system for non-invasively interrogating an in vivo sample for measurement of analytes comprises a pulse sensor coupled to the in vivo sample for detect a blood pulse of the sample and for generating a corresponding pulse signal, a laser generator for generating a laser radiation having a wavelength, power and diameter, the laser radiation being directed toward the sample to elicit Raman signals, a laser controller adapted to activate the laser generator, a spectrometer situated to receive the Raman signals and to generate analyte spectral data; and a computing device coupled to the pulse sensor, laser controller and spectrometer which is adapted to correlate the spectral data with the pulse signal based on timing data received from the laser controller in order to isolate spectral components from analytes within the blood of the sample from spectral components from analytes arising from non-blood components of the sample.

19 Claims, 13 Drawing Sheets

(51) Int. Cl.
 *G01N 21/65* (2006.01)
 *G01J 3/06* (2006.01)
 *G01N 33/49* (2006.01)

(52) U.S. Cl.
 CPC ........... *G01J 3/0218* (2013.01); *G01J 3/0275* (2013.01); *G01J 3/06* (2013.01); *G01N 21/65* (2013.01); *G01N 33/492* (2013.01); *G01J 2003/062* (2013.01); *G01J 2003/064* (2013.01)

(58) Field of Classification Search
 CPC .... G01J 3/1809; G01J 2003/4424; G01J 3/28; G01N 21/65; G01N 33/492; G01N 2201/105; A61B 5/0022; A61B 5/0075; A61B 5/14; A61B 5/7267; A61B 5/1455
 See application file for complete search history.

(56) References Cited

U.S. PATENT DOCUMENTS

| | | | |
|---|---|---|---|
| 7,595,873 | B1 | 9/2009 | Deck |
| 7,595,973 | B1 | 9/2009 | Lee et al. |
| 2002/0133065 | A1 | 9/2002 | Lucassen et al. |
| 2003/0109774 | A1 | 6/2003 | Lucassen et al. |
| 2004/0127778 | A1 | 7/2004 | Lambert et al. |
| 2011/0263043 | A1 | 10/2011 | Livingston |
| 2012/0010513 | A1* | 1/2012 | Wong .................. A61B 5/6847 600/165 |
| 2013/0317328 | A1 | 11/2013 | Ridder et al. |
| 2014/0104611 | A1 | 4/2014 | Watson et al. |
| 2016/0139045 | A1 | 5/2016 | Gulati et al. |
| 2017/0211982 | A1* | 7/2017 | Lenigk ............... G01N 21/8483 |
| 2018/0328786 | A1 | 11/2018 | Lambert |
| 2018/0372632 | A1 | 12/2018 | Min et al. |

OTHER PUBLICATIONS

Communication Pursuant to Rule 161(1) EPC in corresponding EP Application No. 20843013.2, dated May 2, 2023.

Extended European Search Report in corresponding European Patent Application No. 20843013 dated Jul. 3, 2023. 19 pages.

* cited by examiner

FIG. 9
| SOURCE | WEIGHT | SPECTRUM |
|---|---|---|
| HUMAN SUBJECT 1 | W1 | 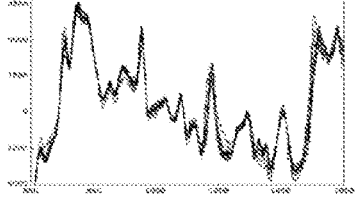 |
| HUMAN SUBJECT 2 | W2 | S2 |
| HUMAN SUBJECT 3 | W3 | S3 |
| HUMAN SUBJECT 4 | W4 | S4 |
| HUMAN SUBJECT 5 | W5 | S5 |
| HUMAN SUBJECT 6 | W6 | S6 |
| HUMAN SUBJECT 7 | W7 | S7 |
| HUMAN SUBJECT 8 | W8 | S8 |
| HUMAN SUBJECT 9 | W9 | S9 |
| HUMAN SUBJECT 10 | W10 | S10 |
| ANALYTE 1 | W11 | 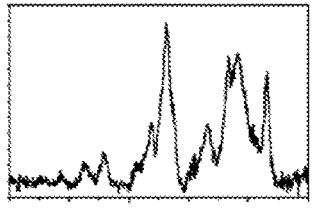 |
| ANALYTE 2 | W12 | 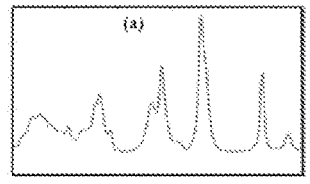 |
| ANALYTE 3 | W13 | S13 |
| ANALYTE 4 | W14 | S14 |

SYSTEM AND METHOD FOR NON-INVASIVE MEASUREMENT OF ANALYTES IN VIVO

CROSS-REFERENCE TO RELATED APPLICATION

The present invention claims priority to U.S. Provisional Patent Application Ser. No. 62/878,074, having the same title, filed Jul. 24, 2019, which is incorporated by reference herein in its entirety.

FIELD OF THE DISCLOSURE

The present disclosure relates to chemometrics, the determination of concentrations of analytes, and more particularly relates to a system and method for non-invasive measurements of analytes in vivo.

BACKGROUND OF THE DISCLOSURE

Many commonly used medical diagnostic devices, such as glucometers, are invasive in that they require blood or other tissue to be drawn from the patient for analytic and/or diagnostic purposes. This procedure can be painful and potentially risky to the patient. In addition, few medical diagnostic devices are applicable across a range of targeted analytes, and generally, samples need to be sent to laboratories for the concentration of multiple analytes to be determined.

Non-invasive chemometric devices have been introduced but these generally possess limited applicability, i.e., they are only useful for determining the concentration of a specific analyte or analyte class, or else they suffer from poor signal-to-noise ratio (S/N), falling short of 90% accuracy versus test standards. As an example of the former, the article "Resonance Raman Measurements of Carotenoids using Light Emitting Diodes" by Bergeson et al. reports on a commercial device that focuses on detection of the Raman line of carotenoids under resonance conditions. The technique disclosed by Bergeson et al. does not generalize to a large range of analytes due to the specific resonance conditions it employs. Other non-invasive techniques including near-infrared spectroscopy have been used for specific analytes (e.g., "Pulse Ox") but such methods have not been sufficiently accurate for many other analytes of interest (e.g., glucose), or when more than one test subject is examined.

What is therefore needed is a non-invasive method for measuring analytes in vivo that is applicable to a wide range of analytes and that can also provide accurate concentration measurements, without requiring calibration to individual test subjects.

SUMMARY OF THE DISCLOSURE

Disclosed herein is a probe for non-invasively interrogating an in vivo sample for measurement of analytes. The probe comprises a laser generator for outputting laser radiation having a specified wavelength, power and beam diameter, a spinning mirror coupled to a driver that is adapted to deflect the laser radiation onto the sample such that a focal point of the laser radiation on a surface of the sample moves over time, reducing the average radiation intensity at any single point on or in the sample, and collection optics positioned to receive Raman signals elicited by impact of the laser radiation at the focal spot on the sample, and emanating therefrom, via the same scanning mirror. The laser radiation directed onto the sample is adapted to elicit Raman signals from the sample which are used to measure the analytes in the sample.

In certain embodiments, the mechanical driver is implemented as a motor that is coupled to and adapted to rotate the mirror such that the laser radiation deflected from the mirror traces a pattern on the sample surface. In other embodiments, the mechanical driver can be implemented as a piezoelectric element that is coupled to and adapted to pivot or vibrate the mirror to deflect radiation in a similar manner to trace a pattern on the sample surface. Other types of mirror drivers can be used. Additionally, it is possible to produce a similar scanning effect by moving the sample rather than the tracking focal points of the laser radiation and the collection optics. In some implementations, the scanning of the laser radiation reduces the average radiation intensity impacting the sample at any single location to less than 0.1 $W/cm^2$.

In certain implementations, the probe further comprises a window with a small mirror at its center, positioned between the laser generator and scanning device. The small mirror redirects laser radiation transmitted from the laser generator along a path to the scanning device, with the Raman signals and Rayleigh scattered laser radiation travelling along a second path, through the window area that is not obscured by the small mirror, and toward a long-pass filter designed to block most (99.999%) of the Rayleigh-scattered radiation at the wavelength of the laser radiation, and also to allow through the Raman signal along the second path. The Raman signals from the sample are then focused by a condenser lens and directed into a fiber that carries the Raman signals and weakened laser radiation to a detection device, which in one implementation, comprises a spectrometer with a TEC-cooled CCD imaging array.

Also disclosed herein is a method for non-invasively interrogating an in vivo sample for measurement of analytes. The method comprises generating laser radiation having a wavelength, power and diameter, deflecting the laser radiation onto the sample such that a focal point of the laser radiation on the surface of the sample moves over time, causing a drop in average radiation intensity at any single point on the sample surface, and collecting Raman signals elicited by impact of the laser radiation at that focal point on the sample, and emanating therefrom. The collected Raman signals are used to measure the analytes in the sample.

In certain embodiments, the laser radiation is deflected by a rotating mirror adapted to deflect radiation onto the sample such that such that the deflected radiation traces a pattern, such as a circle, an oval, a raster scan, on or beneath the sample surface. The average radiation intensity impacting the sample at any single location can be less than 0.1 $W/cm^2$.

In certain embodiments, the method further comprises redirecting the laser radiation along a first path directed toward the sample along which the radiation is deflected by the scanning component. The scattered radiation (both Rayleigh and Raman) travel along a second path that also is deflected by the scanning component toward a filter to remove most of the radiation at the wavelength of the laser along this second path towards the detection device. The Raman signals from the sample are thus directed along the second path toward the detection device such that both a reduced laser signal (Raleigh scattering mostly blocked by the filter) and the Raman signals (not blocked by the filter) are directed into the fiber that carries these signals to the detection device.

In addition, the present disclosure provides a system for non-invasively interrogating an in vivo sample for measurement of analytes. The system comprises a pulse sensor coupled to the in vivo sample adapted to detect a blood pulse wave in the sample and to generate a corresponding pulse signal, a laser generator for generating a laser radiation having a wavelength, power and an original diameter, the laser radiation being directed toward the sample to elicit Raman signals from the sample, a laser controller adapted to turn the laser generator on or off, a spectrometer situated to receive the Raman signals and to generate spectral data from which analyte concentrations can be computed; and a computing device coupled to the pulse sensor, laser controller and spectrometer, the computing device adapted to correlate the spectral data with the pulse signal received from the pulse sensor based on timing data received from the laser controller in order to isolate spectral components from analytes within the blood of the sample from spectral components from analytes arising from non-blood components of the sample.

In some embodiments, the computing device is configured to compute an exponential moving average of the pulse signal and to send a signal to the laser controller for activating the laser generator when the pulse signal obtained from the pulse sensor falls below or rises above the exponential moving average of the pulse signal, such that the spectrometer receives Raman signals during valleys or peaks of the blood pulses.

In certain embodiments, the system further comprises a scanning device adapted to deflect the laser radiation onto the sample such that a surface area on the sample that the laser radiation impacts is greater than the original beam diameter with a corresponding drop in average radiation intensity at any location in or on the sample surface. The wavelength of the laser radiation produced by the laser generator can be selected to elicit resonant enhancement of one or more analytes of interest contained within the sample.

A method for non-invasively interrogating an in vivo sample for measurement of analytes is also disclosed. The method comprises detecting a pulse signal of blood of the in vivo sample, generating laser radiation having a wavelength, power and an original diameter at controllable times (i.e., controlling the frequency and duration the vivo sample is exposed to the laser radiation), the laser radiation being directed toward the sample to elicit Raman signals from the sample, producing analyte spectral data from the Raman signals; and correlating the spectral data with the pulse signal and timing of laser generation so as to isolate spectral components from analytes within the blood of the sample from spectral components arising from analytes within non-blood components of the sample.

In certain embodiments, the method further comprises computing an exponential moving average of the pulse signal, controlling the laser generator to turn on when the pulse signal falls below or rises above the exponential moving average of the pulse signal, wherein spectral data is generated during valleys or peaks of the blood pulses.

In some embodiments, the method further comprises deflecting the laser radiation onto the sample such that a surface area on the sample that the laser radiation impacts is greater than the original diameter with a corresponding drop in average radiation intensity at any location in or on the sample. The wavelength of the laser radiation can be selected to elicit resonant enhancement of at least one analyte of interest contained within the sample.

The disclosure further provides a method of determining analyte concentration from spectral data containing experimental Raman signal data. The method comprises collecting a set of experimental spectral data, generating additional semi-synthetic spectral data by adding variations to the received experimental spectral data, and training a machine learning algorithm (or other model or combination of models) to decipher relevant Raman signals from the spectral data using as a training data set, both the received experimental spectral data and the additional semi-synthetic spectral data.

These and other aspects, features, and advantages can be appreciated from the following description of certain embodiments of the invention and the accompanying drawing figures and claims.

BRIEF DESCRIPTION OF THE DRAWINGS

FIG. 9 is a table including records of spectra and weights associated with specific analyte sources.

DESCRIPTION OF CERTAIN EMBODIMENTS OF THE DISCLOSURE

Overview

Figure 1:
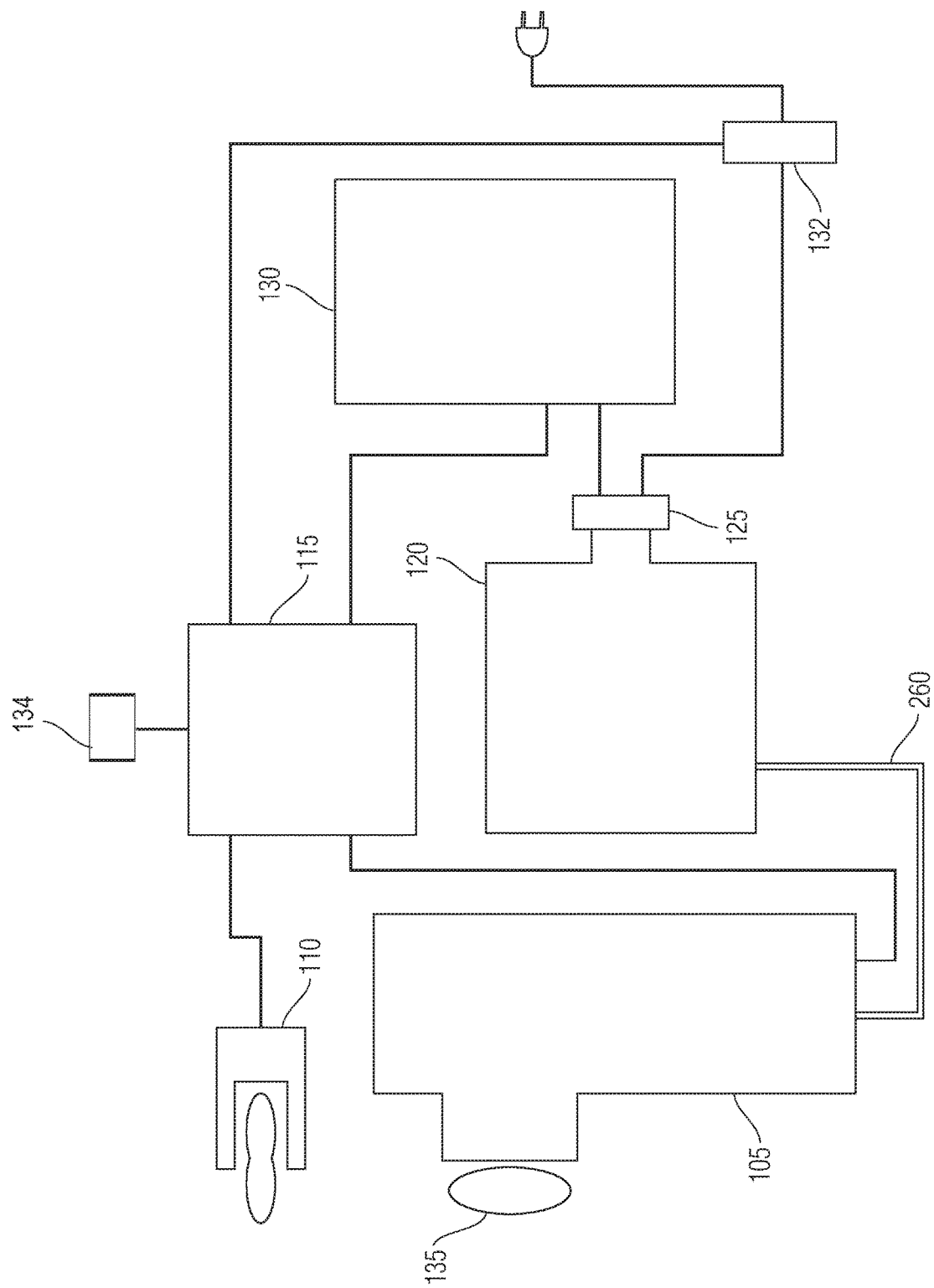
FIG. 1 is a schematic block diagram of the main components of a system for non-invasive measurement of analytes in vivo according to the present disclosure.

A simplified, schematic overview of a system for non-invasive measurement of analytes in vivo is shown in FIG. 1. The components of system 100 include a Raman probe 105, a pulse sensor 110, a laser control unit 115, a spectrometer 120 with a TEC-cooled CCD (thermoelectrically cooled Charge Coupled Device) array 125, and a Host Computer 130. The Host Computer 130 is configured using computer-executable instructions in a known manner to send commands to the laser control unit 115 and to process the measurement data acquired by the Spectrometer 120 and TEC-cooled CCD array 125. A first dedicated DC power supply 132 can be used to provide power to TEC-cooled CCD array 125 and a second dedicated DC power supply 134 can be used to provide power to the laser control unit 115. The Raman Probe 105 is configured to generate laser radiation, which is directed toward an in vivo biological sample 135 (e.g., a part of a human patient such as a finger) for the purpose of "interrogating" the sample containing analytes of interest. The sample 135 may contain a wide range of analytes of interest for medical or other purposes including, glucose, A1C, cholesterol, fatty acids, AGEs, carotenoids, and bilirubin, among others.

The radiation emitted from the Raman Probe "interrogates" the sample 135 in the sense that the radiation directed onto the sample interacts with the chemical elements within the sample, such that the sample generates responsive signals (by fluorescence, Rayleigh scattering, and Inelastic "Raman" scattering) that can be detected by measuring instruments, such as the Spectrometer 120 with the TEC-cooled CCD array 125. The Raman probe 105 can be embodied in a variety of ways including for example, using lasers with different wavelengths so as to elicit resonant enhancement of specific analytes, and using various mechanisms to enable high powered-lasers to be used for the purpose of capturing large numbers of photons without exceeding safe $W/cm^2$ limits (e.g., a scanning element or rotating mirror). In Raman probes, the captured Raman signals tend to be weak. While certain analytes are strongly reactive to specific wavelengths due to the phenomenon of resonance and yield signals that are relatively strong and easy to detect over a broadband fluorescent background, not all analytes of interest can be easily detected by this phenomenon, and unwanted background fluorescence can overwhelm the weak signals produced by non-resonant Raman scattering from the analytes of interest.

In one of the embodiments discussed below, the Raman probe 105 is designed to interrogate the sample so as to generate molecular response signals by Raman scattering. Raman signals have the advantage that they are specific to analytes and thus have the characteristic of "signatures"; however, Raman signals also have the notable disadvantage that they tend to be quite weak, and often orders of magnitude weaker than background fluorescence. Moreover, the sensor of the Spectrometer 120, which, as noted, can be embodied as a TEC-cooled CCD array 125, can introduce additional sources of noise due to pixel gain variability, thermal or "dark" current variations across pixels (such as "hot pixels", which is an extreme case of such variation), random shot noise (which is generated by the randomness of the arrival of photons at the sensor and is therefore stochastic), and other factors. Even in the absence of such additional sources of noise, the direct output of the spectrometer may not be obviously revealing in terms of the concentration of the analytes of interest due to the overlap of signals from the hundreds, if not thousands, of distinct analytes present in the sample. In most instances, the data processing phase performed by the Host Computer 130 turns out to be crucial. It has been discovered by the inventor that conventional data processing techniques such as partial least squares regression (PLS) and principal component analysis (PCA) cannot reliably or efficiently sort out or detect the targeted weak analyte signals. Instead, specific data processing algorithms, including but not limited to machine learning algorithms and non-negative matrix factorizations, informed by known physical relationships and spectra acquired from individual analytes, are required to suitably decipher the analyte signals from the spectrometry data.

Accordingly, all of the components of the system 100, from the Raman probe 105 to the spectrometer 120 and TEC-cooled CCD array 125 to the Host Computer 130 need to be configured together to meet the task of detecting the weak signals of interest, against a background of strong, unwanted signals (including noise and broadband fluorescence), and thereby determine the concentrations of specific analytes present in the sample non-invasively. The disclosure below accordingly includes refinements in probe, spectrometer and data processing design that improve analyte level determination accuracy to achieve non-invasive measurements with clinically acceptable accuracy.

Figure 2:
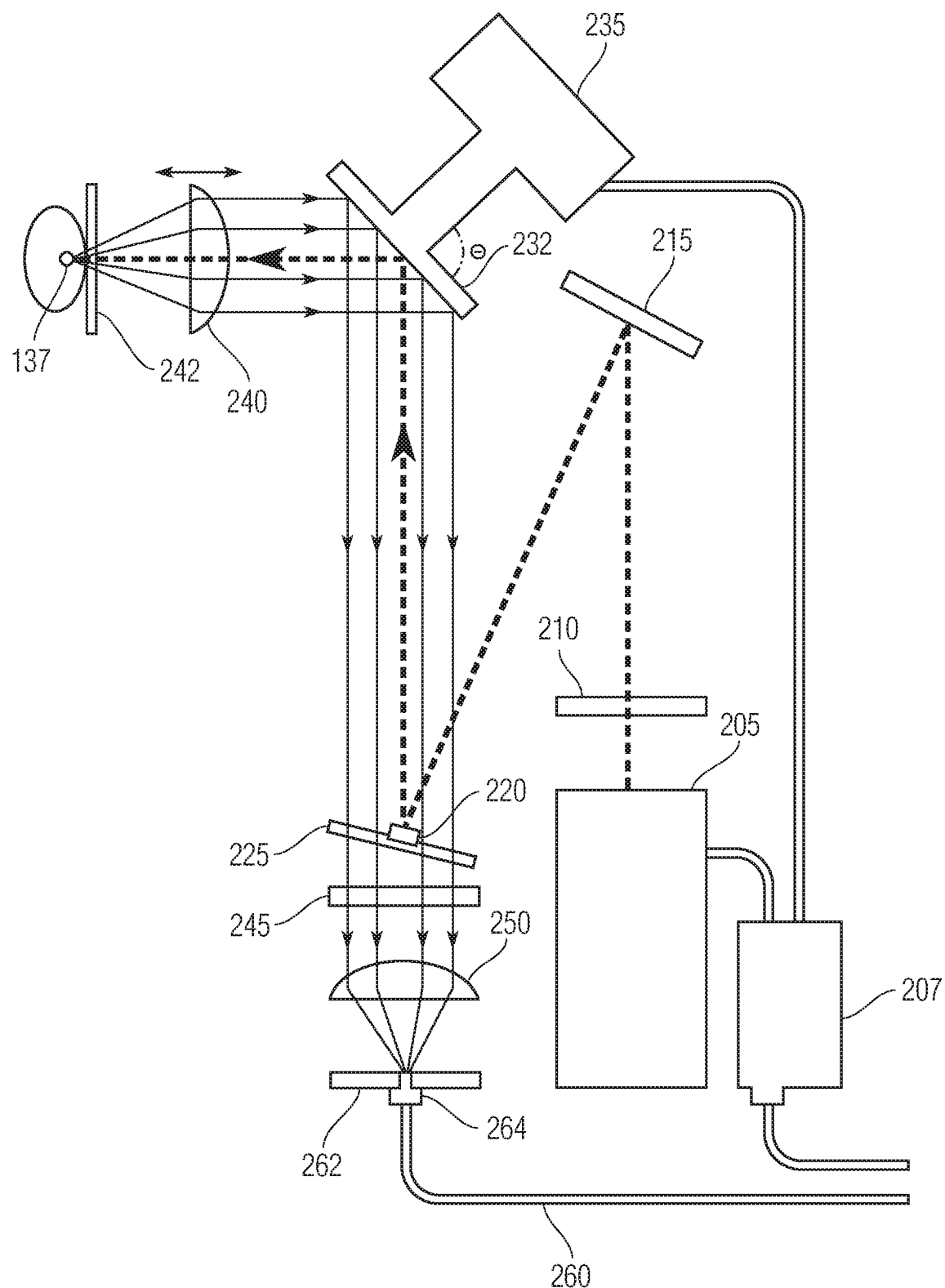
FIG. 2 is a schematic diagram of an embodiment of a Raman probe for use in the system for non-invasive measurement of analytes in vivo based upon Raman spectroscopy according to the present disclosure.

FIG. 2 is a block diagram of an embodiment of a Raman probe 105 that can be used in a system for non-invasive measurement of analytes in vivo based upon Raman spectroscopy according to the present disclosure. In Raman spectroscopy, incident radiation is scattered by a molecule inelastically, meaning that the energy of a photon scattered in this manner is slightly less (usually) or slightly more than the energy of the incoming photon. Spectroscopically, the scattered radiation includes a strong line of the same frequency as the incoming photon (from regular elastic "Rayleigh" scattering) and weaker lines on either side of the strong line ("sidebands", from inelastic "Raman" scattering) called the Stokes and anti-Stokes lines. The strengths and frequency ranges of the Stokes and anti-Stokes lines can be used in molecular identification. It is noted that the embodiment of the probe shown in FIG. 2 is merely one implementation of a probe for use with the system; those of skill in the art would appreciate that numerous modifications can be made to be the components and their specifications as required to target certain analytes, improve signal-to-noise ratio (S/N), reduce fluorescence, reduce certain types of noise, improve modularity (e.g., use of a fiber-coupled laser assembly), etc.

Referring again to FIG. 2, the probe 105 includes a number of components starting with a laser generator assembly 205 ("laser assembly"). The specific wavelength of the laser radiation emitted by the laser assembly 205 can be selected based upon the specific analytes of interest which can be stimulated to resonate at certain wavelengths. Since resonance greatly enhances the signal-to-noise ratio, the wavelength of the laser can be selected to elicit such resonances. Resonant enhancement is often observed near peaks in the absorption spectrum of an analyte. Glucose, for example, is known to have absorption peaks in the near infrared (NIR) range and laser wavelengths in this range may be able to elicit resonant enhancement for glucose and related analytes having absorption peaks in this range. When the specific analytes of interest are not predetermined, or the resonance of the analytes of interest are unknown, the laser wavelength can be based on other optical considerations, for instance, longer wavelength lasers are known to produce less fluorescence at the cost of weaker signals. As suppression of fluorescence is a concern in distinguishing weak Raman spectral lines, use of longer wavelengths is indicated in some instances in which the S/N ratio is low due to high levels of background fluorescence. In some implementations, shifted-excitation Raman techniques can be employed to allow for removal or "cancellation" of the fluorescence baseline. One embodiment of this technique employs a broadband source like an LED to stimulate fluorescence for establishing a baseline that can be subtracted from the spectra obtained with the narrow-band source (the laser).

Another embodiment involves the use of two or more lasers of slightly different wavelengths; Raman signals shift in frequency along with the lasers, but the fluorescence tends to remain the same, allowing for its estimation and removal.

The laser assembly 205 of the probe (FIG. 2) is controlled by the laser control unit 115 (shown in FIG. 1) which can be configured to control the timing and length (in time) of laser pulses, or more generally the timing at which the laser generator is turned on and off. Laser radiation emitted by the laser assembly 205 is transmitted through a line (band-pass) or a short-pass filter 210 which passes the laser wavelength and removes any spectral output from the laser generator that deviates from the central laser wavelength. From the line filter 210, the beam is transmitted to a mirror 215. From the mirror 215, the laser beam travels to a second mirror 220, which is embedded in a window 225, that reflects the laser beam to mirror 232.

Mirror 232 is coupled to a mechanical driver 235 that is adapted to rotate, pivot and/or vibrate the mirror in response to an electrical activation signal. Instead of a mirror 232, the scanning device can include an angled filter. Additionally, the mechanical driver 235 can be implemented in alternative ways. For example, the mechanical driver can be a motor with a shaft that is coupled to the mirror 232 or it can include a piezoelectric element is configured to cause the mirror to move or vibrate. The purpose of the mechanical driver is to alter the reflection of the laser from the mirror in such a manner that the focal point of the laser beam as well as the focal point of the collection optics scan in lockstep over multiple points on the sample 135, preferably in a prescribed pattern. In this way, the diameter of the beam focused on the sample remains small and tight, but the average intensity of radiation to which the sample is exposed (in terms of Watts/cm$^2$) at any single location is reduced for a laser beam of given power, relative to a stationary beam. It is noted that in some implementations the sample 135 can be moved or shifted to accomplish a similar purpose, although this is typically a less convenient technique when dealing with in vivo samples. This is analogous to moving a candle flame across one's hands: there is no burn; however, if one leaves the candle (and hand) in a fixed position, a severe burn is the result. Both the mechanical driver 235 and the laser assembly 205 can be activated by a driver unit 207.

In order to make this work, as the focal point of the laser beam is scanned via mirror 232, the focal point of the collection optics must track the scanned laser's focal point so that the focal point of the excitation laser and the focal point of the collection optics are at all times precisely coincident. At any single point in time, the laser beam illuminates a small spot on (or in) the sample from which the scattered light can be efficiently collected and sent down a fairly small fiber. This dual scanning (implemented by the rotating mirror in the current embodiment) allows a higher-power laser to be employed than would otherwise be the case, without burning or damaging the sample. If the laser were focused continuously on a single small spot on the sample, only low power could be used: a high power laser would damage the sample from excessive heating. Thus, to reduce the average power incident at any one location on the sample, and avoid such damage, the focal points are scanned. Since the sample has thermal mass, sufficiently fast scanning can result in an average power at each point on the sample that can be made far lower than the instantaneous peak power. This means a higher power laser can be used to elicit the Raman effect, yielding stronger signals and thus a better signal-to-noise ratio. Also, more representative sampling of the sample is achieved.

This method thus keeps the demand for etendue manageable, even low, while allowing the use of higher laser power with efficient collection of the scattered light from the sample. Scanning the sample with tightly focused laser beams and receiving the Raman signals with tracking confocal collection optics is a way to achieve efficient capture of Raman scattered photons and thus make an "end run" around the law of etendue (without violating it). The focal spot on the sample is at all times kept small enough for the returning Raman signals to be focused into a small fiber without significant loss, while a high-power laser can be used in the manner of a high etendue system, such as one having a beam spreader or diffuser on the laser (to prevent sample burn) and a collection system with large fiber bundles and large low F/#optics (to collect signals from the resultant large illuminated area). It is again emphasized that for this method to work, the illumination optics and the collection optics need to be confocal (focused on the same spot) at all points in time. In the depicted embodiment, the rotating or vibrating mirror 232 is placed near the objective lens, in the path of both the collimated laser beam, and the collimated signals returning from the sample. This placement of the mirror 232 ensures that the focal points for both the laser optics and the collection optics track each other closely.

The scanned radiation reflected from the mirror 232 is directed onto a focusing (also known as an Objective) lens 240 and then onto a sample 135. The sample can be placed in a vial or on a glass window 242 to provide for consistent focus at the desired depth. In one example, rotation of the mirror 232 by the motor assembly 235 causes the focal point inside the sample (which may be a finger placed on a glass slide) to scan in a pattern which ensures that the average radiation at any one location in or on the sample is sufficiently low so as not to cause damage or interfere with accurate measurements. In some implementations, for instance in those tests in which the sample is a finger of a patient, a pulse sensor 110 is positioned on a second nearby finger to take the pulse of the patient for reasons that will be explained further below.

At the sample, the incoming laser radiation interacts with component analytes and induces Raman scattering. The scattered Raman radiation ("Raman signal") is transmitted back through a lens 240 which collimates the Raman signal, and then transmitted to the scanning device mirror 232 at which the Raman signal is reflected back toward the window 225 with the embedded mirror 220. The Raman signal passes through the unobscured area of the window 225 to a long pass filter 245. The long pass filter 245 is designed to block a majority of laser wavelength radiation (the intensity of which would produce overwhelming interference and could even damage the CCD array) while letting the weak Raman signals pass. It should be understood that the resulting Raman signals include unwanted broadband fluorescence, some amount of noise, as well as a very small portion ($10^{-6}$ or so) of radiation at the laser wavelength. The Raman signal transmitted through the long pass filter 245 then passes through condenser lens 250 which focuses the collimated Raman light into the end of the fiber. Although not shown in FIG. 2, if needed a small diffuser/homogenizer may be placed just in front of the fiber bundle so as to homogenize the incoming Raman signal in order to reduce spatial variation noise at the fiber tip (different fibers in the bundle getting different levels of illumination). The Raman signal is ultimately passed into a fiber or fiber bundle 260 which is situated at the output port 262 of the probe.

In certain implementations, the fiber bundle may consist of a 7-strand bundle with a circular arrangement of fibers at the probe end, and a linear arrangement of fibers at the spectrometer end, the latter designed to optimize coupling to the spectrometer's input slit. The fiber bundle 260 in this instance is secured to the probe using an SMA905 connector 264. In other instances, the fiber bundle may be a large diameter "light pipe" such as is used for illumination in microscopy; "light pipes" come in the form of very large fiber bundles and also in the form of large-diameter liquid light waveguides. Use of light pipes require different connectors to be used, both in the probe and in the spectrometer, due to their large diameters.

The spectrometer used in the current implementation described below has large F/1.4 optics and a large CCD sensor, and can handle a long 10 mm slit, and hence can make beneficial use of a "light pipe" or, preferably, a large circular-to-linear fiber bundle to capture a large number of photons per second from a large diameter target area on or in the sample. In other words, this is a high-etendue system. The fiber bundle or light pipe transmits the Raman signals from the Raman Probe 105 to the spectrometer 120 which separates the wavelengths of the incoming Raman signals and generates a low noise, high resolution image of the separated wavelengths, that is, the spectra. Note that in implementations that employ a large fiber or fiber bundle, beam scanning can be eliminated; a beam expander can be placed directly after the laser to spread the beam, since the photons from the resultant larger diameter spot on the sample can be efficiently captured and transmitted into a sufficiently large fiber (i.e., a fiber with a diameter roughly on par with the diameter of the illuminated spot focused on the sample). With a small diameter fiber, such as must be used with many commercial spectrometers, a small beam diameter must be used for efficient photon collection, and hence beam scanning is employed to distribute the beam energy over a larger area of the sample. However, even with a high-etendue spectrometer, scanning can still enable higher laser power and more representative sampling of the sample, making for an even more sensitive analytical instrument.

Spectrometer

Figure 3:
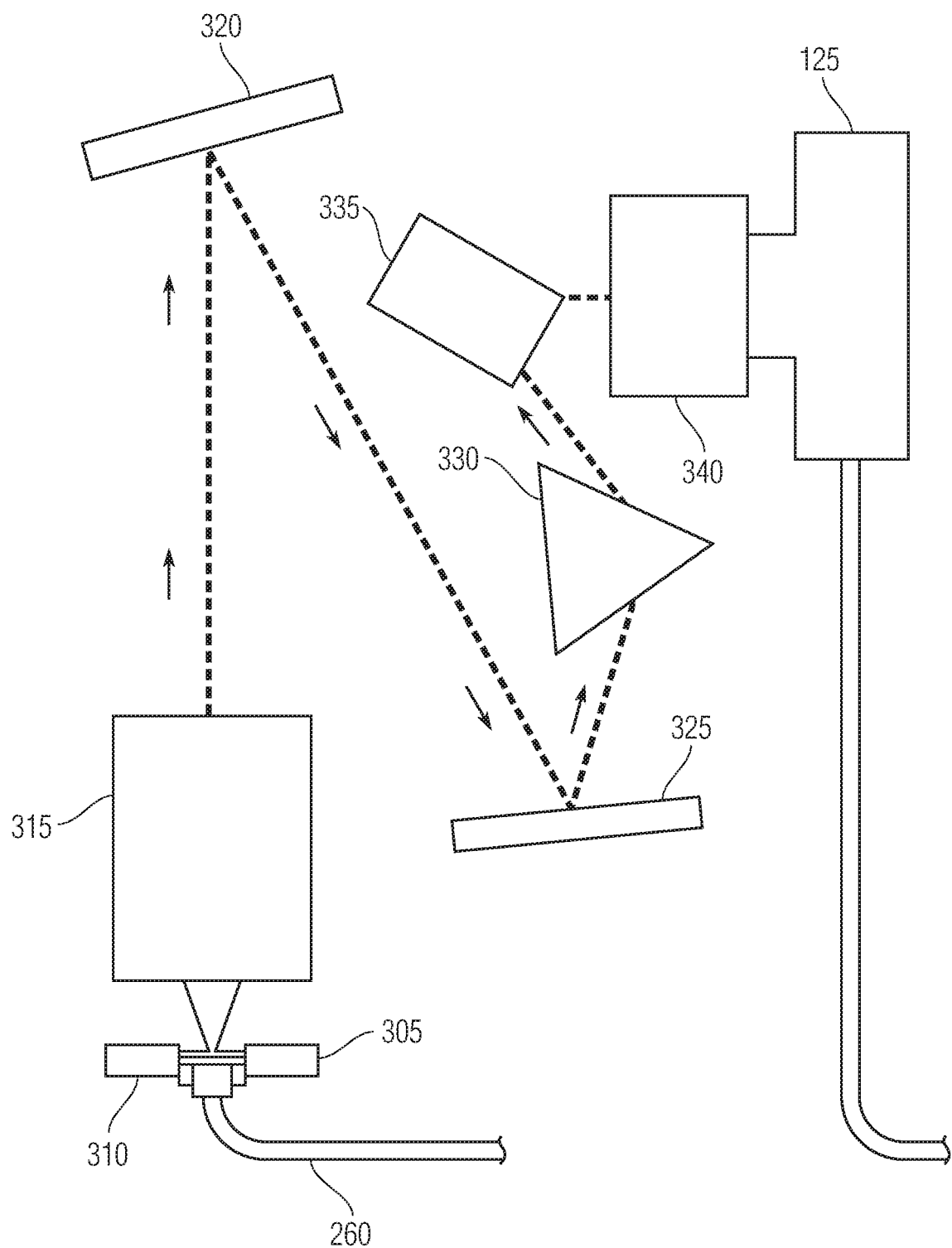
FIG. 3 is a block diagram of the main components of an exemplary spectrometer that can be used in a system for non-invasive measurements of analytes in vivo according to the present disclosure.

FIG. 3 is a schematic block diagram of a spectrometer that can be used in the context of the disclosed systems and methods. The fiber bundle or light pipe 260 shown in FIG. 2 transports the light from the Raman Probe 105 to the input of the Spectrometer 125 which comprises a fiber connector 305 terminating at a slit 310. The size of the slit can be adjusted depending on the configuration of the Spectrometer as described below. A collimating lens 315 is positioned to collimate the Raman signal radiation coming through the slit 310 and to direct the collimated radiation toward a first mirror 320 which in turn redirects the incoming radiation to a second mirror 325. The radiation is reflected from the second mirror 325 to a cross-dispersing prism 330. The prism separates and deflects the incoming wavelengths of the Raman signal radiation horizontally according to wavelength. The prism performs the order separation that is required with an echelle design. Radiation then travels to a diffraction grating 335, which again redirects the radiation according to wavelength, this time vertically, toward a focusing lens 340. The focusing lens 340 focuses the radiation diffracted by the grating 335 onto the TEC-cooled CCD detector 125. The spectrometer is constructed so that it can easily be reconfigured as a single order (non-echelle) spectrometer, allowing a far longer slit to be employed at the expense of total spectral coverage.

The TEC-cooled CCD imaging device 125 includes an array of pixels, each of which generate electrical charges proportional to the amount of radiation (number of photons) that they accumulate subject to various sources of noise discussed below. The electrical charges can then be read out to produce a spectrographic image indicating the wavelengths, and their strengths, present in the light entering the spectrometer, in this case, the Raman signal radiation. The grating 335 can be swapped depending on needs. In one particular embodiment, grating 335 can be implemented using an 1800 ln/mm holographic grating (non-echelle configuration). In some implementations the grating can be swapped for an echelle grating. In certain implementations the Spectrometer 120 can be configured with a volume phase holographic grating, a large fiber bundle and a very long slit (e.g., a 10 mm slit with a circular-to-linear fiber bundle) to obtain exceptional light-gathering power at the expense of spectral coverage (although the spectral coverage is still more than adequate for the present application as described below). In other embodiments the Spectrometer can be equipped with an echelle grating to maximize spectral coverage. To accommodate the echelle grating, the Spectrometer is restricted to a smaller-diameter fiber (e.g., 600 μm fiber and a matching slit). In this embodiment, the spectral range extends from the near ultraviolet well into the near infrared (350 nm to 1100 nm) in a single frame without any moving parts. A software-configurable Spectrometer can be designed to selectively implement both of the above-described embodiments. For example, a plurality of gratings, including both holographic gratings and an echelle grating, can be arranged on a rotating element that is driven by stepper motor, or similar device, so that the gratings can be swapped in or out of the optical path of the Spectrometer. Additionally or alternatively, any of the plurality of gratings installed in the optical path can be adjustably rotated by another motor to change the grating angle with respect to the optical path in order to modify spectral coverage.

One of the main challenges to achieving high performance in non-invasive chemometrics of the kind envisioned herein lies in obtaining the requisite instrumentation characteristics. More specifically, the characteristics of the probe and spectrometer significantly affect the likelihood of obtaining stable and accurate results. Experiments have shown that it is necessary to use a spectrometer that has high resolution, reasonable spectral range, high etendue (e.g., the ability to use a large diameter fiber bundle so as to capture more photons per second), and high dynamic range in order to detect and accurately measure analyte concentrations, especially with analytes that are weak Raman scatterers and in the presence of high levels of sample fluorescence.

The resolution of a spectrometer determines the maximum number of spectral peaks that the spectrometer can resolve. The spectrum can be divided into "bins" and a high-resolution spectrometer can thus be characterized as having narrow bins. One of the consequences of having narrow bins is that there is less noise (including random shot noise and unwanted broadband fluorescence) per bin without attenuation of any valid narrow-band Raman signals that fit inside the bins. Less noise with equally strong signals implies a higher S/N ratio. Tests have demonstrated that for a 532 nm laser, a resolution in a range of about 0.05 nm to 0.2 nm performs well. For longer wavelength lasers, e.g. 980 nm, tests have shown that a resolution between 0.2 nm to 0.8 nm is acceptable, as at longer wavelengths, the same Raman frequency shift translates into larger wavelength change. High resolution is especially beneficial in situations with narrow signals (common in Raman scattering) in the context of high levels of broadband fluorescence. Another benefit is that specific analytes can more easily be identified due to reduced interference from nearby peaks generated by other analytes. It is noted that it is difficult or impossible to compensate for inadequate resolution using procedures such as smoothing, deconvolution, drizzling, stacking or increasing exposure length.

A reasonably wide spectral range (achieved by a spectrometer such as described herein, even in a non-echelle configuration) is also beneficial as it allows more signals to be detected. In general, a spectral range from about 200 $cm^{-1}$ to about 3600 $cm^{-1}$ is desired. For example, glucose has multiple Raman signals ranging from well below 500 $cm^{-1}$ to over 3000 $cm^{-1}$; it is beneficial for the spectral range to be wide enough to cover the range of useful Raman signals. As with resolution, it is difficult to compensate for insufficient spectral coverage. It is noted, however, that if a specific range of wavelengths is targeted for a specific analyte (e.g., glucose), hardware requirements can be simplified by only sampling a few relevant subsets of the targeted range. In many cases an optimal set of narrow-band subsets will not be known prior to testing; therefore, to determine the optimal wavelength and filter requirements for a given analyte initially, spectral coverage sufficient to encompass all relevant spectral information is necessary. Once such initial data is obtained for one or more analytes, algorithms can be designed and employed to determine optimal filter sets for measurements of a limited set of analytes with a miniaturized device.

Other spectrometer characteristics can significantly affect performance as well. Many high-performance spectrometers detect radiation using charge-coupled devices (CCDs) which convert photons into electric charge. CCDs tend to produce noise in proportion to the temperature at which they are maintained because of thermodynamic movement of electrons. This is called "dark current". To achieve low noise, it is useful to cool the CCD used in the spectrometer with thermoelectric coolers to a temperature range of −20° C. or lower. Another important consideration is etendue, or light-gathering power. A high etendue means that more photons may be captured per second from a larger area, which translates into a better S/N for a given integration period. In the probe embodiment described above, effective etendue can also be increased (or be further increased) using the scanning device which spreads the illumination over a larger area of the sample. The real etendue can be increased by use of a larger fiber diameter; a higher fiber diameter enables a wider beam containing more photons to reach the spectrometer (assuming the spectrometer can handle it). In general, techniques are employed to ensure that the photon throughput, or sensitivity, of the system is sufficient to obtain Raman signals strong enough for analysis.

The dynamic range of the spectrometer is another factor that can comes into play in improving overall S/N, especially when there is a large fluorescent background, as is typically the case for biological materials and, especially, for non-invasive in vivo measurement. A CCD with a high dynamic range is able to take longer integrations without pixels becoming saturated (for instance, due to strong broadband fluorescence), enabling more photons to be captured with less readout noise. A large dynamic range permits fewer CCD readouts per unit time, and total readout noise can be thus reduced for a given total photon count, improving the overall S/N. In the current implementation, high dynamic range is achieved by using a spectrometer design that spreads the slit image (the signal) for each wavelength over numerous pixels, yielding a high "effective well depth" roughly equal to the number of pixels times the individual pixel well depth.

Apart from the considerations in setting the characteristics of the spectrometer (e.g., resolution, spectral range) and certain operating conditions (e.g., dynamic range), calibration of the spectrometer for wavelength and for variations in sensitivity from wavelength to wavelength or pixel to pixel, is necessary to achieve good performance. Calibration for sensitivity is particularly important in the Raman spectrometry context, and particularly when there are high levels of smooth background fluorescence. Large levels of background fluorescence interacting with variations in pixel to pixel (wavelength to wavelength) sensitivity can produce high levels of spiky noise that resemble genuine Raman signals. The fluorescence is broadband and smooth, not spiky, so that if the wavelength to wavelength sensitivity is precisely calibrated, the background fluorescence as it appears in the spectrogram will be smooth and can thus be more easily separated from the Raman signals. So-called "flat fielding", i.e., correcting for sensitivity variations over the image frame or spectrum, is often ignored in most publications outside the world of astronomy. Besides wavelength to wavelength sensitivity, there are a number of other noise or interference sources intrinsic to spectrometer operation. There is bias or offset which varies with temperature, and dark current which varies with temperature and from pixel to pixel, with some pixels ("hot pixels") being affected by temperature to a greater extent than others. There are also variations in pixel sensitivity, such as noted above, which tend to be stable for a given CCD. These "noise" sources can generally be removed by calibration processes and the associated mathematical operations involving dark frames, flat fields, and calibration lamp frames, which can be used to determine the gains, offsets, and dark currents of the pixels. Although these are referred to here as "noise", many are not stochastic in nature, but have consistency and repeatability and can thus be "calibrated out" (and hence the noise is designated with quotes). Once calibration is performed, images can then be corrected according to the known gains and dark currents of the CCD pixel set because of their consistency and repeatability. Stochastic noise is essentially unpredictable and cannot be calibrated away; it is true noise (without the quotes). An example of stochastic noise is so-called "shot noise" or "Poisson noise" which derives from the impact of photons randomly striking the detector similar to the random clicking of a Geiger counter.

The spectrometer is designed, at the cost of introducing, or not correcting for, certain aberrations in order to: 1) eliminate as many optical elements as possible to reduce losses and stray light; 2) maximize flexibility, resolution, and etendue; and 3) simplify mechanical construction, as long as the introduced or uncorrected aberrations can be mathematically reversed. More specifically, in some implementations, optical aberrations are employed or permitted that result in little or no loss of information and that can be mathematically reversed without the introduction of significant artifacts. One example of such aberrations are curvatures in the slit images (see FIG. 7A). It has been found that introducing slants (non-rectilinearity) in the slit images, and then compensating for the aberration mathematically once the images are digitized, actually yields enhanced spectrometer performance. Analysis demonstrates that such enhancement can also be obtained in spectrometer designs that have rectilinear slit images merely by rotating the camera (CCD image) so that the slit images appear slanted, with an optimal angle, on the image plane. Allowing such aberrations to intrude can allow for simpler optics, better resolutions, less stray light, and better throughput, among other potential advantages. Conversely, poor resolution, stray light and low throughput result in irreversible losses of information that cannot be mathematically undone. The aim is to aggressively minimize the latter type of optical aberrations, by introducing, where possible, the former type of mathematically reversible aberrations that cause no actual loss of information.

Slanted slit images also enable finer-grained sampling, so-called "super-resolution", and the use of deconvolution (if necessary), with far fewer artifacts resulting from aliasing of higher-frequency spatial components into the main band of interest. This is analogous to time series sampling, audio signal processing, and the process of "drizzling" in astronomical image processing. Drizzling, in particular, is a digital image processing method for the linear reconstruction of dithered images to compensate for under-sampling from a large field of view. The dithered images are produced by moving a telescope slightly in random directions for a few pixels between exposures. The dithered images are combined using an algorithm that weights images by the statistical significance of each pixel. The drizzling algorithm is able to remove the effects of geometric distortion, rotation, and translation, while preserving photometric validity. Slanted slits, which can be implemented in different way ways, such as by rotating the camera slightly, provide similar effects in that the central wavelengths of the pixels occur at intervals smaller (with long slits, much smaller) than those covered by the actual horizontal pixel spacings. This is because pixels in each row of the image are slightly shifted in their central wavelengths relative to other rows. This shift can be considerably less than the center-to-center wavelength differences between successive pixels in any single row. When the pixels are rearranged, and then "drizzled" onto a much finer grid, a far higher effective sampling rate is attained. The result is a better-sampled, smoother, lower noise spectrum.

Introducing slants (non-rectilinearity) in the slit images, and then dealing with this aberration mathematically once the images are digitized, yields significantly enhanced spectrometer performance over the performance achieved when the aberrations are corrected optically. Analysis demonstrates that such enhancement can also be obtained in spectrometer designs that have rectilinear slit images by rotating the camera (CCD image) so that the slit images appear slanted, with an optimal angle, on the image plane. There arc two primary benefits that derive from slanted slit images. One benefit is finer grained sampling in the wavelength domain, as mentioned above: The effective sampling interval in the wavelength domain decreases with increasing slit length. A thick fiber bundle and very long slit provide high etendue and long slit images on the CCD. The long slit images can yield a very fine-grained spectral sampling. Since the resolution (based on pixel size) remains constant, the finer sampling amounts to oversampling, with the degree of oversampling being proportional (given an optimal slit angle) to the length of the slit images (measured in pixels). Such oversampling makes it possible, with appropriate deconvolution algorithms, to achieve sub-pixel resolution in the final spectrum (so-called superresolution) without introducing significant artefacts (such as Gibbs phenomena or "ringing"). A second benefit conferred by slanted slit images, together with their mathematical reversal in the digitized images, is a far greater robustness in the face of column defects, "popping" pixels, and other imperfections that commonly occur in CCD imaging devices. This is especially true when working with lower cost large format CCD chips. Likewise, cosmic ray strikes are more easily removed and have less impact on the final spectrum extracted from the image. Pixel gain or sensitivity variations also tend to be averaged out due to the numerous pixels contributing to each wavelength bin in the final observed spectrum.

Furthermore, distributing specific wavelengths over multiple columns of CCD elements by slanted slit images avoids or dramatically reduces the impact of column variations or defects. This is especially true for long slits, with slit images covering hundreds or thousands of pixels, as might be encountered in a high etendue system such as described herein. This may be achieved as a result of aberrations in the optics as discussed above. Distribution of specific wavelengths over multiple columns of CCD elements can also be achieved by simply rotating the CCD imager slightly and adjusting the spectral extraction software to match.

For applications in which a small number of analytes are of interest, the required spectral range of the spectrometer can be narrowed significantly. This allows the spectrometer to be designed for miniaturization. For example, for narrow spectral range applications, components of the spectrometer such as filter wheels and customized chips can be used in place of larger components such as gratings and large CCD arrays.

Pre-Scan Calibration

In light of the issues discussed above, it is necessary to perform pre-scan calibration procedures on the spectrometer before obtaining spectra from samples to remove as much non-stochastic "noise" as possible. A first part of the pre-scan calibration process is dark current correction. Dark current correction is performed with all light sources off and shutters closed. It is done to determine whether the pixels of the CCD array exhibit current variation even in the absence of stimulation by a light source (all CCDs do to some extent, although sufficient cooling can reduce dark current to negligible levels). Dark correction proceeds by first capturing a set of "dark frames" with the CCD array and then compensating for dark current variations among the pixels in the data array by subtracting out those found in the dark frames. Dark correction can also be performed in other ways. For example, dark frames can be interspersed with data frames from actual Raman spectra or other sources. Again, spectral images are dark-corrected by subtracting out the dark frames after removing cosmic ray artifacts.

Figure 5:
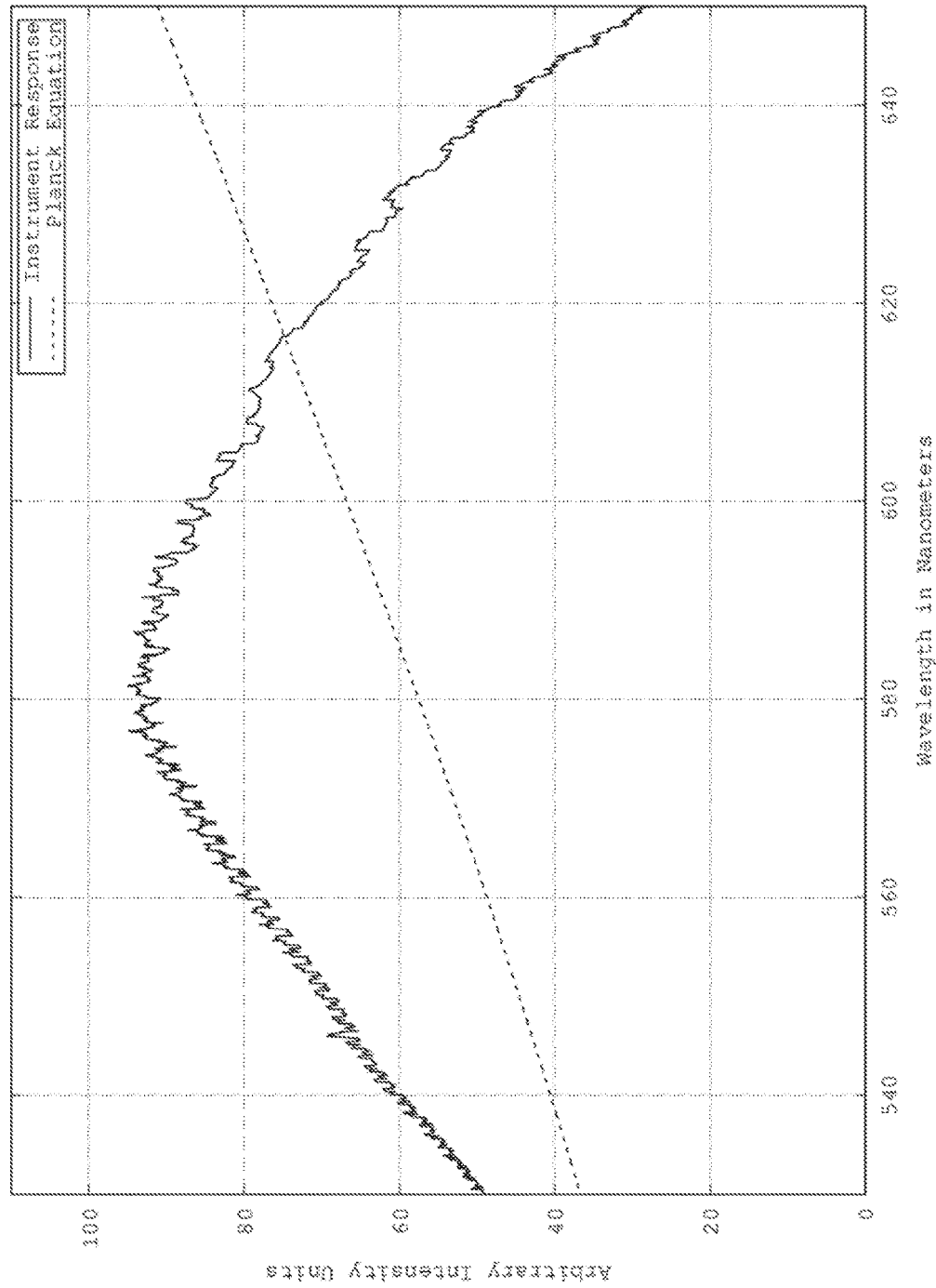
FIG. 5 is an exemplary observed spectrum of a tungsten lamp and the theoretical spectrum according to Planck's equation.

In a second step, systematic noise due, for example, to wavelength-to-wavelength sensitivity variation is removed. This can be done by so-called flat fielding using a tungsten lamp, although other procedures can be used alternatively or additionally. Tungsten lamps have a well-known spectrum that matches well with the spectrum predicted by Planck's equation for black body radiation. FIG. 5A shows an exemplary observed spectrum from a Tungsten lamp along with the expected Black-Body spectrum at 2600° K calculated from Planck's equation. Note, the curves differ from one another: this is because of variations in system sensitivity due to the spectral responsivity of both the optics and the CCD over a range of wavelengths. The calibration process finds a calibration weight function $W(i)$, for all spectral bins (i) having an uncalibrated spectral photon count $S(i)$, such that $W(i) * S(i)$ matches $P(i)$, the expected black body radiation at the wavelength corresponding to spectral bin (i) and the temperature (T) of the tungsten lamp filament.

In the flat-fielding procedure, radiation from a tungsten lamp is detected by the spectrometer and two or more spectral data curves are generated for the tungsten lamp radiation. From these spectra S(i), the weight calibration function W(i) for each bin are determined. Once the weight calibration function W(i) is generated, it can be used in subsequent procedures to correct for the wavelength sensitivity variation in the optics and in the TEC-cooled CCD array and to remove such variation from the spectrometer data. Thereby, this above-described calibration process corrects the spectrometer (and even the probe) before running scans on samples for systematic "noise" including dark current, wavelength-to-wavelength sensitivity variations, and bias.

Figure 6A:
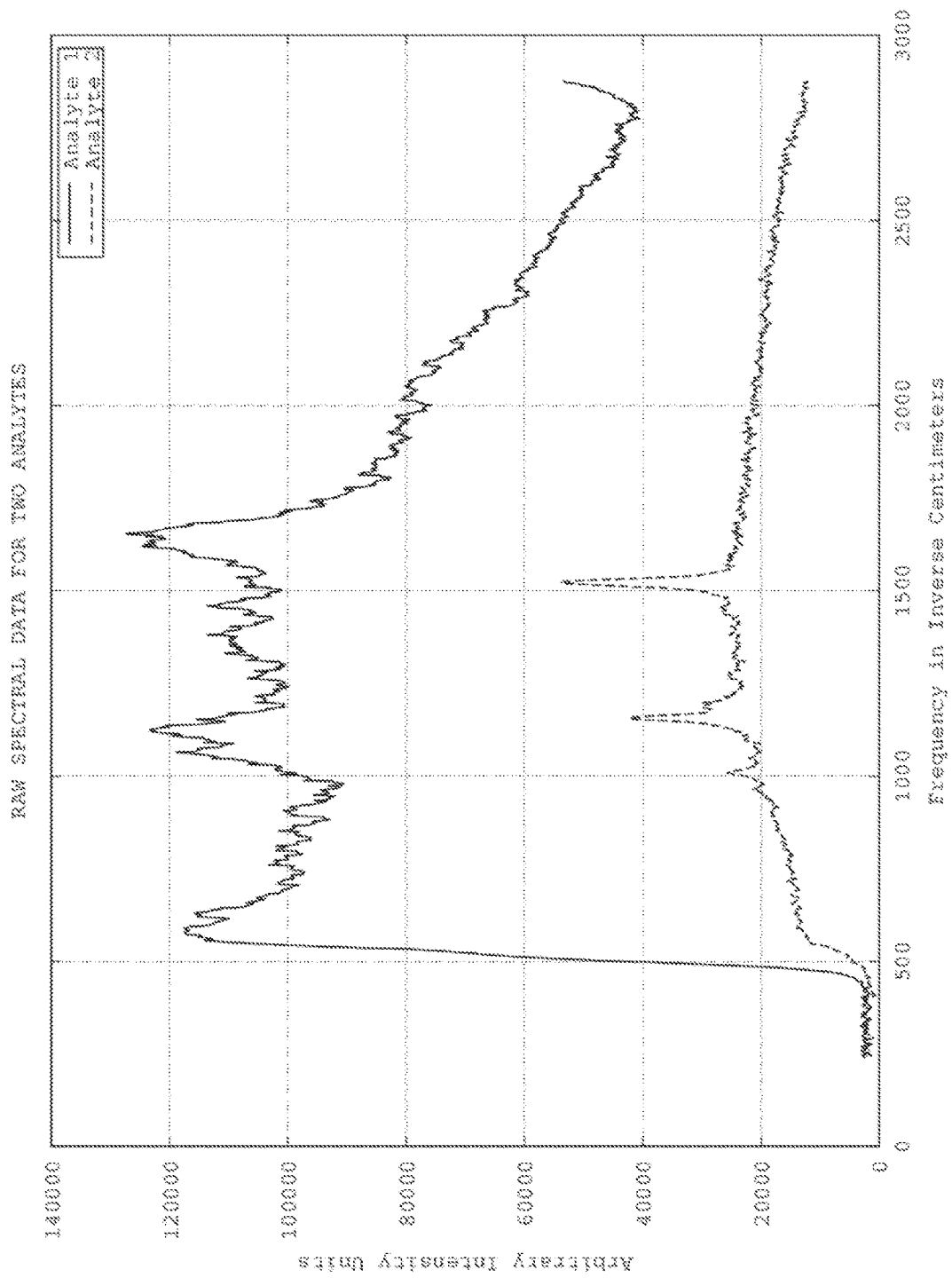
FIG. 6A shows dark-corrected spectra of glucose and Annatto carotenoids obtained without flat fielding using an embodiment of the Raman system disclosed herein.
Figure 6B:
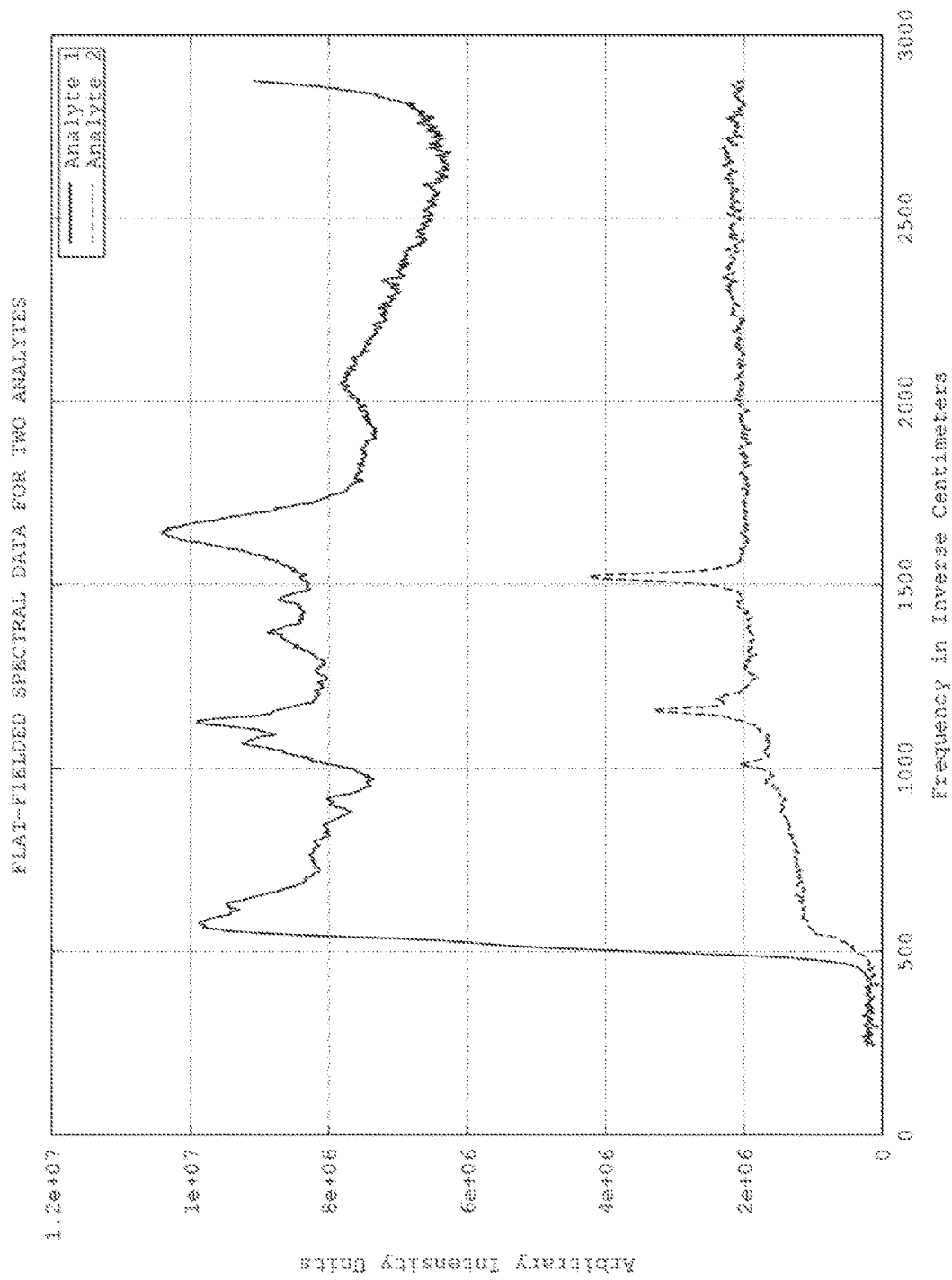
FIG. 6B shows the spectra of FIG. 6A after flat fielding calibration using a tungsten lamp and the Planck equation.

FIGS. 6A and 6B illustrate the effect of calibration on spectral data. FIG. 6A shows raw spectra of two analytes which are only corrected for dark current and not calibrated using flat fielding. The upper trace is a spectrum of glucose and the lower trace is a spectrum of Annatto carotenoids. FIG. 6B shows spectra based on the same underlying image data after both dark correction and flat-field calibration. A comparison of FIGS. 6A and 6B shows that the noise level, especially for glucose, is vastly lower in the flat-fielded data. Also, the slopes and peak amplitudes have changed: for instance, one can see a peak for glucose around 2100 inverse centimeters that is not evident in the data prior to flat-field calibration. The accuracy of relative peak intensities is an important factor in modeling analytes because distortion in the relative intensities of peaks at different wavelengths can, in extreme cases, make some analytes indistinguishable. Flat field calibration helps ensure that relative peak intensities are physically correct.

Figure 7A:
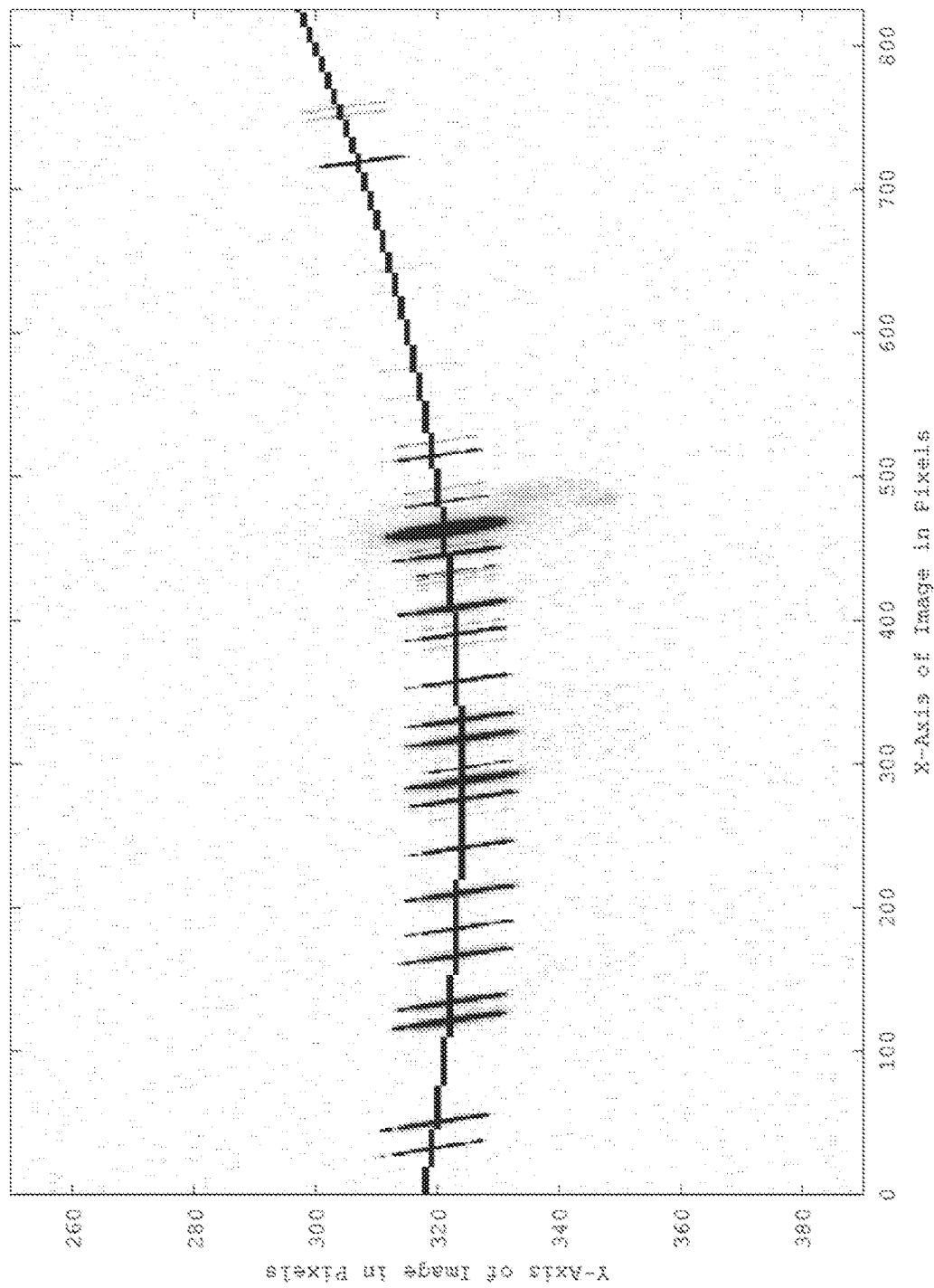
FIG. 7A shows a raw dark-corrected spectrum of a neon lamp obtain using an embodiment of Raman system disclosed herein.

An additional calibration procedure needs to be performed for wavelength using a neon-argon lamp other emission-spectrum source. FIG. 7A shows a raw (dark-corrected only) spectral image taken from a neon-argon calibration lamp. The spectral image contains sharp slit images associated with neon emission lines (presented as a negative image in which darker equates with more photons). The image also depicts a properly fitted "order tracing curve", which is the smooth curve drawn through the slit images. The order tracing curve can be obtained during an initial calibration procedure and then used thereafter to extract the spectrum as long as the spectrometer configuration has not been changed. The order tracing curve only needs to be recalculated rarely, due to drift. In taking the image, cooling was turned off, binning was set to 4×4 (low resolution, low dynamic range mode), and only a small subset of the entire CCD image is shown.

Figure 7B:
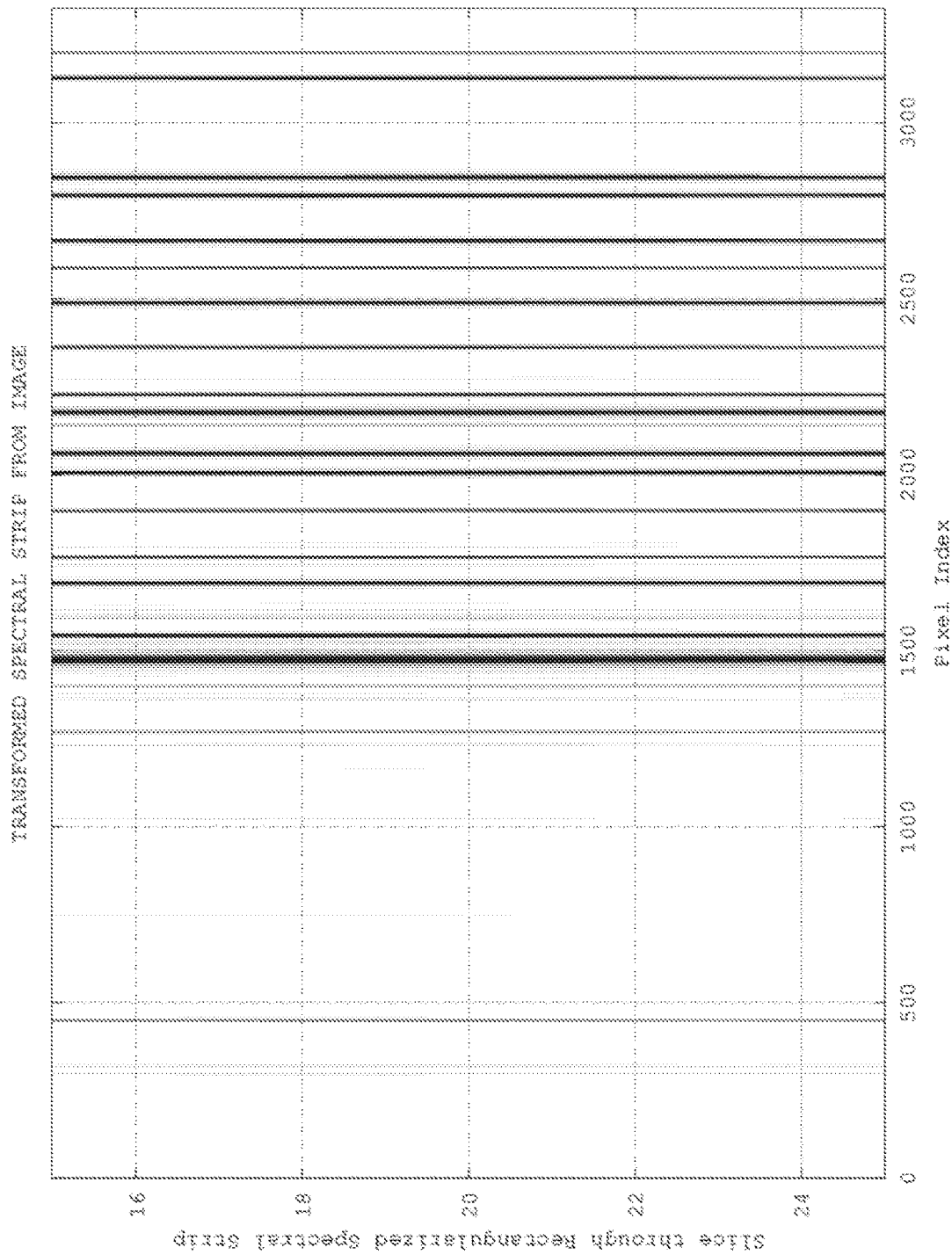
FIG. 7B shows the spectrum of the neon lamp of FIG. 7A corrected for optical aberration.

FIG. 7B shows the spectral image of the neon-argon lamp after correction of aberrations due to the optical configuration of the spectrometer are made. Only a subset of the remapped pixels is shown. In general, many pixels contribute to each wavelength or spectral line, and the number of pixel contributions may be increased by use of a longer slit and larger fiber bundle. This effectively allows numerous independent channels or observations to contribute to the intensity measurement at each wavelength, contributing to reduced noise and greater effective dynamic range.

Figure 7C:
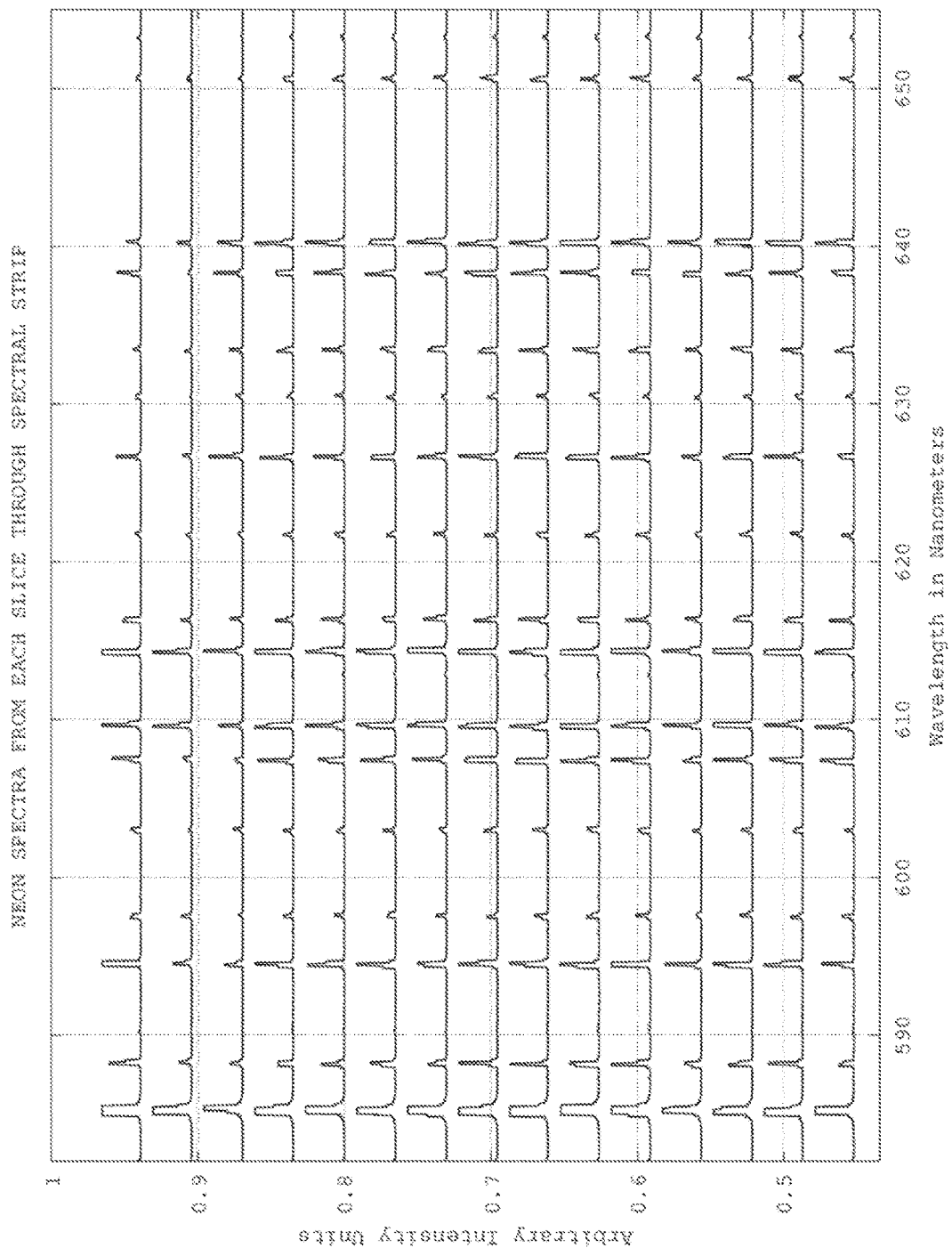
FIG. 7C shows the underlying data of the neon spectrum of FIGS. 7A and 7B obtained from different slices (row or columns) of the CCD detector of the spectrometer.
Figure 7D:
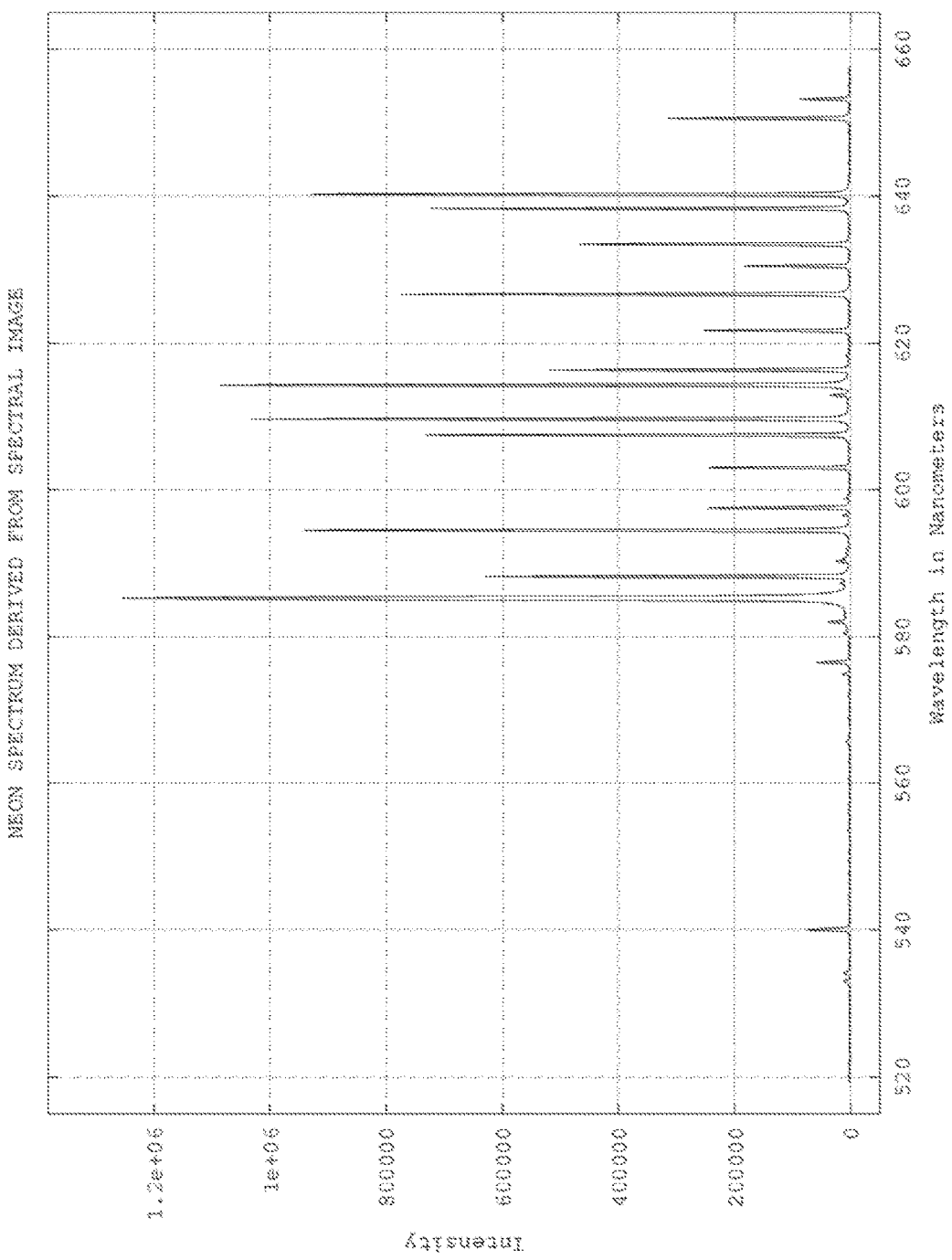
FIG. 7D shows a calibrated neon emission spectrum obtained by summing the slices in FIG. 7C and calibrating for wavelength.

FIG. 7C shows the same data as shown in FIG. 7B presented as a set of spectrum plots from different "slices" (rows or columns) of pixels of the CCD detector. Only a small subset of slices is shown in FIG. 7C. The slices exhibit some intensity variation due to spaces between the fibers in the bundle employed (a Thor Labs circular to linear 7-core bundle), as well as due to variation in the illumination entering the individual fibers in the bundle at the probe end. These variations can be corrected using a diffuser or homogenizer at the end(s) of the fiber. Variations in fiber core illumination change with source positioning, and this alters the sensitivity pattern, which in turn, can interfere with stable flat fielding. FIG. 7C also shows that some pixels are saturated (at their maximum value). Because of the many pixels contributing to the intensity measurement at each wavelength, the effect is not very evident in the final spectrum plot of the neon calibration lamp shown in the FIG. 7D. This plot is calculated by summing the slices shown in FIG. 7C. Calibration for wavelength is done by fitting a polynomial to map the pixel index to the wavelength in nanometers. The plot of FIG. 7D shows an excellent fit between NIST data on neon and argon emission lines and the observed peaks (the standard error is less than 5 picometers despite the saturated pixels). The X-axis in this plot is in nanometers. It is noted that inverse centimeters, as used in Raman analysis, is a measure of the frequency difference between the laser and the signals (sidebands); it is calculated as inverse_centimeters=10000000/laser_in_nm−10000000/Raman_sig_in_nm. The X-Axis can be configured to show inverse centimeters instead of nanometers if desired.

Data Processing

As indicated in FIG. 1, the spectrometer 120 is coupled, via a direct or wireless communication channel, to a Host Computer 130. Via this connection, the Spectrometer 120 transmits Raman spectrometry spectral data obtained from samples to the Host Computer 130 which is configured to process the spectral data. The Host Computer 130 is also coupled to laser control unit to which it can send command signals and also receive information concerning the timing of laser pulses as well as the blood pulse wave signal. The computing device can be configured with various software tools to execute algorithms and perform mathematical operations such as determining differentials on the spectral data received from the spectrometer (Spectrometer, FIG. 1).

In many applications, the in-vivo analytes of interest are present in the blood, and signals arising from surrounding soft tissue, interstitial fluid, and bone are sources of interference. In the field of pulse oximetry, this problem is addressed by using pulse wave amplitudes rather than total measured signal. Signals arising from blood are distinguished from other sources based on the fact that blood signals are oscillatory during a pulse due to changes in arterial/vascular volume. Accordingly, variations in the measured spectrum characterize arterial/vascular blood only. By analyzing only the oscillating component of the measured spectrum, and discarding the temporally constant component, the analytes present in the blood can be calculated. Application of this technique to Raman spectrometry has not been accomplished to date because of the difficulty in measuring pulse waves, with a periodicity of less than 1 second, using a CCD array designed for the long exposures, measured in minutes, that are required for detecting weak Raman signals. Shorter exposures are not feasible in the Raman context using a photon-counting CCD device since the resulting readout noise would overwhelm the relatively weak Raman signals. Additionally, the process of reading out a large CCD array can itself be a fairly slow process in a low-noise imaging device.

Figure 4:
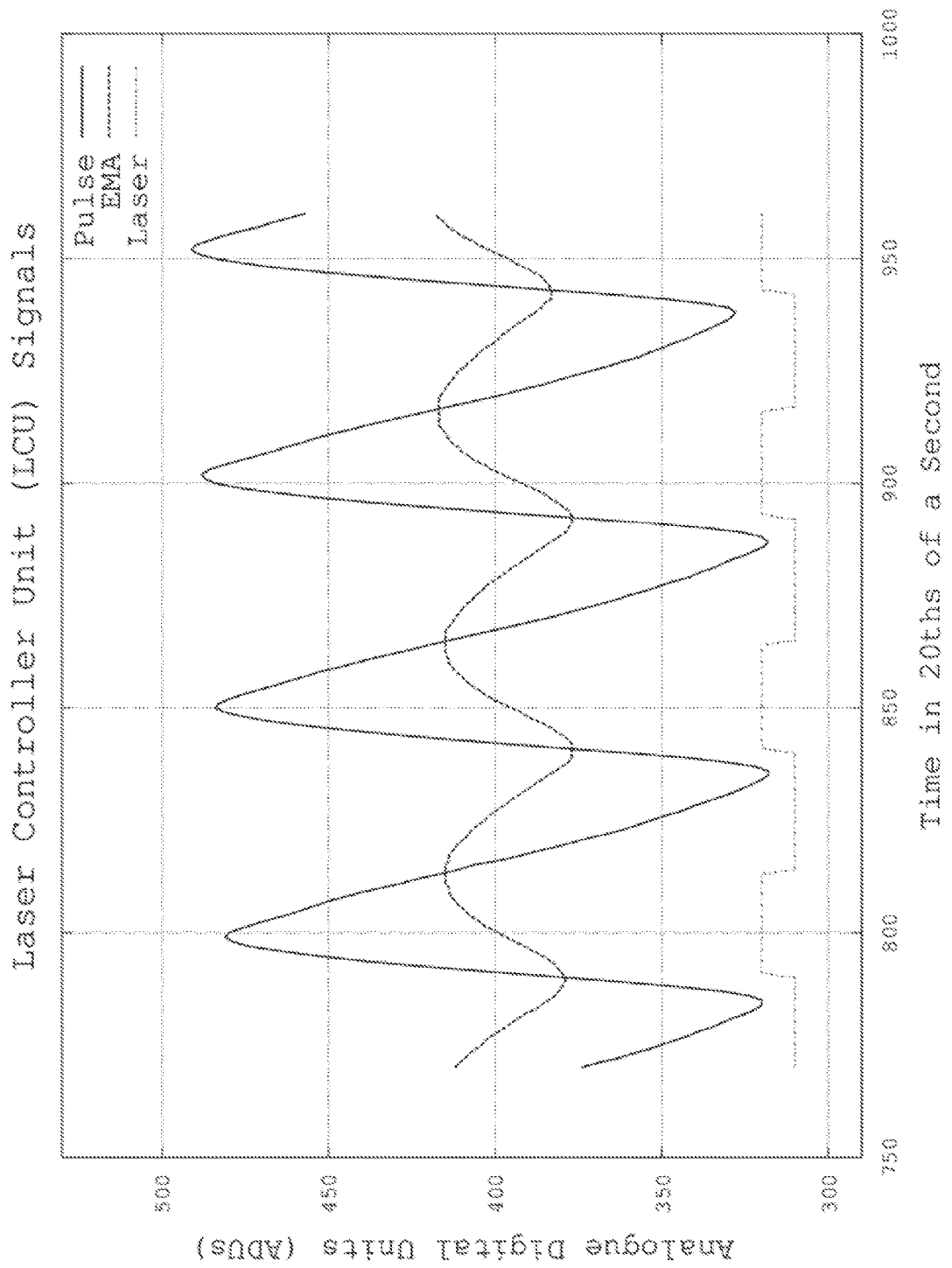
FIG. 4 is a graph showing a pulse wave, exemplary laser activation and pulse wave exponential moving average over time, illustrating a method of capturing Raman spectral data from an in vivo sample containing blood according to an embodiment of the present disclosure.

The present disclosure provides a method to enable the pulse wave amplitude to be measured in a Raman spectrometry context using an ordinary CCD imaging device. The method is illustrated by way of a graph of a pulse signal in FIG. 4. The pulse signal 405 is obtained from the pulse sensor 110 (shown in FIG. 1). FIG. 4 also shows the laser activation signal 410. The laser control unit 115 controls the laser to turn on an off in synchrony with the pulse signal as instructed by the Host Computer 130. The laser activation signal 410 is shown as a square wave signal with on and off periods. In this case depicted, the laser is on when the pulse signal is above its exponential moving average, that is, when blood volume is high. The exact timing of the start of the laser on/off periods is set in conjunction with readings taken from the pulse sensor which is coupled to the laser control unit. In the first exposure (CCD integration), the laser is triggered to turn on at points at which the pulse signal 405 rises above the exponential moving average (ema) 415 of the measured pulse signal 405, and to turn off when the pulse signals falls below the ema. During the next exposure, the laser is triggered in the reverse manner to turn on when the pulse signal 405 falls below the ema signal 415 and turn off when it rises above the ema. In other words, in the first exposure (which may range anywhere from 10 to 100 seconds or more) the laser is turned on only near the peaks of the pulse waves and in the second exposure (having the same integration period as the first exposure), the laser is turned on near the valleys of the pulse signal. The Raman signals from the sample are therefore induced by the laser only during peaks (first exposure) or valleys (second exposure) of the blood pulses and the signals do not get averaged out over the entire pulse oscillation by the CCD detector. By then subtracting the spectra obtained from the second exposure (laser on near valleys) from the first exposure (laser on near peaks), meaningful Raman signals deriving from the blood analytes can be detected, and Raman signals from soft tissue, bone, etc., "cancelled out". When actually performing real-life measurements, the sequence of exposures described above is repeated multiple times in order to increase the signal to noise ratio.

An alternative technique provided by the present disclosure for pulse wave amplitude measurement in a Raman spectrometry context using a CCD array employs laser radiation of different wavelengths to enable one to obtain "pulse high" and "pulse low" data within a single exposure, and thereby significantly reduce the effects of drift. Two different laser sources are used that have wavelengths that are close to each other, for example, 1 nm apart, but still measurably distinct. The laser sources can be different sources manufactured to center on different wavelengths, or they can be identical laser sources running at slightly different temperatures. It is known that laser wavelength varies with temperature of the source, and the temperature of the sources can be easily adjusted with simple TEC cooling elements to provide two lasers having slightly different wavelengths. The two lasers, referred to herein for convenience as "laser A" and "laser B", having wavelengths shifted by a small amount, induce Raman signals (Stokes and Anti-Stokes lines) that are also shifted by the same amount, allowing the Raman spectra produced by lasers A and B to be distinguished. In contrast, background fluorescence that appears in the Raman spectra produced by lasers A and B, being smooth, remains almost the same between the shifted spectra; the fluorescence does not shift.

In this method, laser A and laser B are alternately switched on and off, for example, with laser A on/laser B off, followed by laser A off/laser B on, and so forth. In one implementation, laser A is controlled to switch on (and laser B off) at the peaks of the pulse signals, and laser B is controlled to switch on (and laser A off) at the valleys of the pulse signals. However, Raman spectra from both laser A and laser B are obtained in the same CCD exposure time window. This results in a 2X "multiplex advantage" compared with the single-wavelength method described earlier. The Raman spectra taken using laser A and laser B are subtracted from each other, which eliminates the background fluorescence radiation that the spectra share between them, leaving the Raman signals. Raman signals and fluorescence from the skin are identical, albeit shifted, with both lasers, and so can be mathematically canceled out. As the lasers are switched relatively quickly, on the order of one second or less, there is little time for the sample characteristics to drift (due to slow changes in average blood flow, finger temperature, movement, and so on). Low drift in turn enables substantially complete fluorescence cancelation, since the levels of fluorescence radiation appearing in the respective spectra have almost no time to change, as well as cancelation of Raman signals originating in the skin and fixed tissues. With proper mathematical processing, the Raman signals originating in the blood can be separated from the multiplexed data. This switched laser arrangement is similar to Shifted Excitation Raman, which is sometimes used to cope with high levels of fluorescence, but adapted to also permit separation of blood signals from signals originating in the skin, bone, or other fixed tissues.

As with pulse wave amplitude-based measurements, in order to obtain stable calibration across individuals given differences in skin pigmentation, soft tissue, and other factors, it is necessary to make use of differential or relative measurements of analytes when using Raman data. In one technique, a set of blood analytes that produce strong signals in a stable manner are used as references or baselines. In blood, hemoglobin often serves as a one good reference analyte. In this case, measurements of other analytes in blood are then taken relative to hemoglobin. This technique sidesteps problems due to differences in blood volume, tissue transparency and other factors that have individual and temporal variability. In the literature, many attempts at non-invasive NIR as well as Raman-based analyte measurement have failed due to an inability to get the techniques employed to generalize from one individual to another, or even from one time period to another within one individual.

Augmentation of Data Set Using Semi-Synthetic Data

Even if the spectrometer is designed optimally in terms of resolution, light-gathering ability, and dynamic range, and after all relevant noise reduction, calibration, and pulse wave lock-in procedures have been performed, deciphering Raman peaks in the data output from the spectrometer can be a challenging task due to relative weakness of Raman signals, the numerous signals from the many analytes present, the overwhelming fluorescent background, and various forms of noise remaining, even after the aforementioned measures have been taken.

To address this problem, conventional mathematical procedures including multiple regression, partial least squares (PLS) and principal component analysis (PCA) have been employed in the related art to pick out the Raman signals within the spectrometer data relevant to the quantitative measurement of one or more analytes. These procedures have not been up to the task, in general, of determining analyte concentrations with sufficient reliability or accuracy. This is largely due to the fact that such techniques generally attempt to reduce the dimensionality of excessively collinear data sets by selecting highly redundant features of the data as being of predominant importance. However, because Raman spectra contain a plethora of highly distinct features, any number of which can be of importance in detecting the presence of particular analytes, dimensionality reduction based on total variance or correlation is not an efficient approach in Raman analysis.

The present disclosure employs one or more data processing techniques, which can include machine learning algorithms as known in the art that "learn" through refining weights applied to input data to iteratively approximate known output values. The algorithms employ weights that are obtained by analysis of an augmented data set. The augmented data set includes i) spectra obtained from blood samples taken from a number of subjects; ii) spectra obtained from pure or mixed known analytes; and iii) semi-synthetic data created from a weighted sum of i) and ii) or by other means. It is often difficult to obtain a large number of blood and pure analyte samples to construct a sufficiently large data set for training the algorithms used to detect specific analytes. By augmenting the sample data with semi-synthetic data, a much larger data set can be obtained than would otherwise be possible. The theoretical underpinning that enables this augmentation is the fact that, in the absence of chemical interactions between analytes, Raman spectra are additive. That is, if a particular sample spectrum A shows a Raman peak of amplitude $Y_i$ at frequency X and sample spectrum B shows a Raman peak of amplitude $Y_2$ at the same frequency X, a combined sample spectrum C obtained from a sample having 50% from A and 50% from B, will have a peak corresponding to the linear combination of the two amplitudes, i.e., $(Y_{1+}Y_2)/2$. This feature allows any number of semi-synthetic linear combinations of the underlying data to be generated and treated as original samples (e.g., thousands or tens of thousands of semi-synthetic spectra).

An example of how blood sample spectra and pure analyte spectra can be combined to generate semi-synthetic spectral illustrated with reference to FIG. 9 which shows a table of records of spectra and weights associated with specific analyte sources.

According to FIG. 9, samples have been taken from 10 human subjects (HUMAN SUBJECT 1, HUMAN SUBJECT 2, etc.). Samples have also been taken from 4 known analytes (ANALYTE 1, ANALYTE 2, etc.), so that there are 14 samples in total. The exact number of human subjects and analyte samples is merely exemplary and different numbers of each category can be used. For each of these samples (Human subject 1-10, Analyte samples 1-4) Raman spectra $S_1$, $S_2$. $S_{14}$ are obtained using the system and methods described above. Alternatively, standard spectra can be used for one or more known analyte samples when available. A few exemplary spectra appear in the last column FIG. 9 (i.e., $S_1$, $S_{11}$ and $S_{12}$); these are shown for illustrative purposes only and should not be taken to represent accurate Raman spectra.

Figure 8:
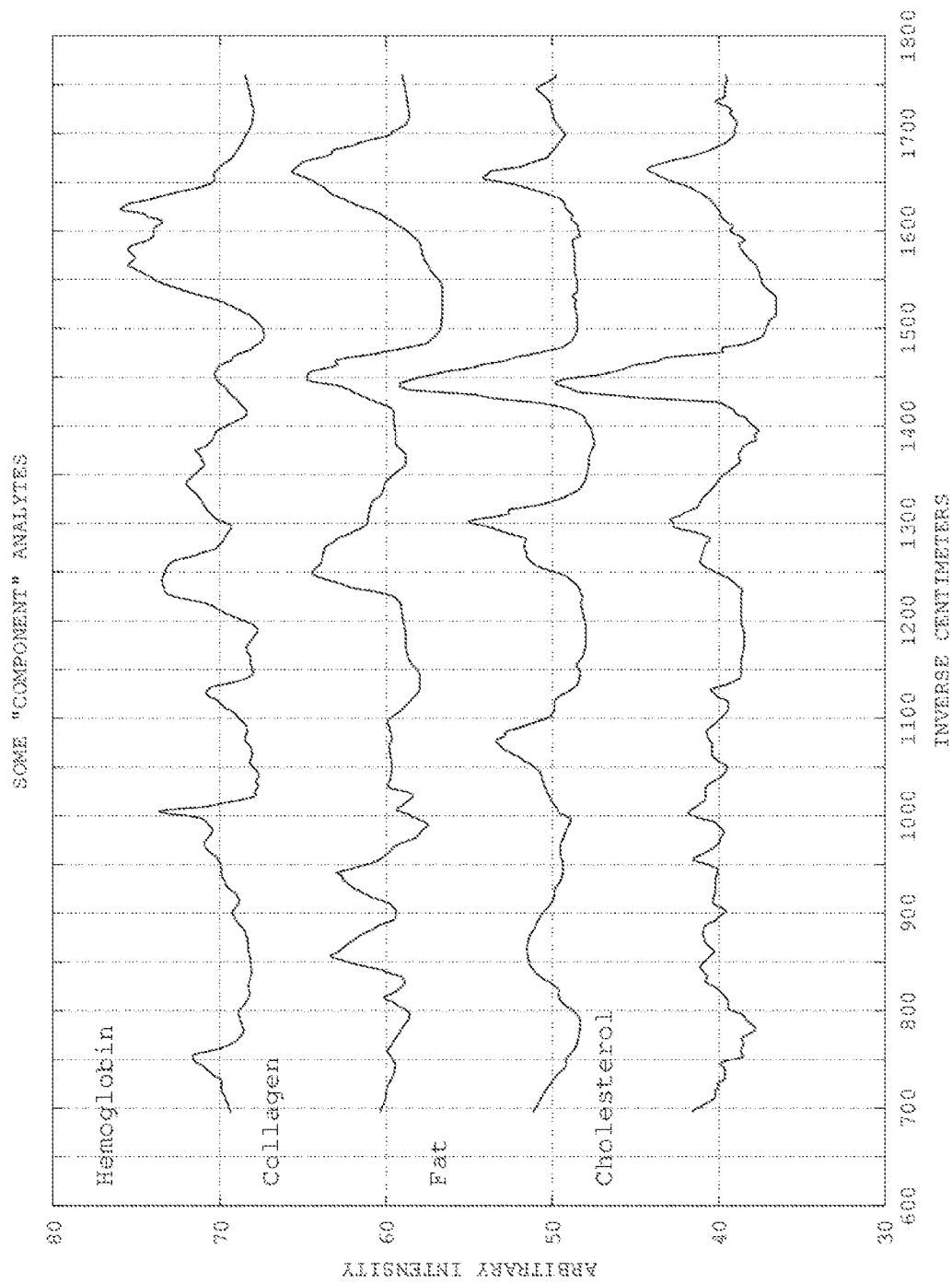
FIG. 8 shows Raman spectra of certain analytes commonly found in in vivo samples including hemoglobin, collagen, fat and cholesterol.

FIG. 8 shows spectra of certain analytes commonly found in in vivo samples including hemoglobin, collagen, fat and cholesterol. The spectrum for hemoglobin includes peaks at 1228, 1562, 1580 and 1621 $cm^{-1}$. It is found that the peaks at 1562, 1580 and 1621 increase, while the peak at 1228 decreases with increasing long-term exposure to glucose. This indicates that A1C and other effects of glycation on hemoglobin can be measured using Raman spectroscopy. Hemoglobin also serves as a reference analyte for use in the differential measurement methods. The spectra of the four analytes show peaks that overlap or are close to one another. For example, collagen, fat and cholesterol show peaks at approximately 1440-1450 $cm^{-1}$. In cases of overlap, the ratio of the amplitudes at such peaks provides useful information. A peak at a given wavelength reflects a particular chemical bond, for example, C=C or C=O. The spectrum of a molecule with a different ratio of C=C bonds to C=O bonds, for instance, will show peaks with amplitudes roughly proportional to the number of bonds that generate a signal at the wavelength.

Since it is useful to have amplitude ratio comparisons for signals at very different wavelengths, it is important to properly flat-field the system so that the sensitivity across wavelengths is constant and calibrated.

The second column of table includes a set of weighting $W_1, W_2 \ldots W_{14}$. The weighting are random values that sum to one (1). A semi-synthetic sample spectrum (sample number 15) is generated as the weighted sum of spectra the 14 source samples. In other words the spectrum of sample 15 ($S_{15}$) is equal to $W_1*S_1+W_2*S_2+W_3*S_3 \ldots W_{13}*S_{13}+W_{14}*S_{14}$. Further samples $S_{16} \ldots Sn$ can be generated in the same way using different random weighting $W_1 \ldots W_{14}$. In this manner an enlarged data set augmented by semi-synthetic data as described above can be used in training neural networks, non-negative matrix models and/or other procedures to improve the accuracy of analyte detection from Raman spectra.

Chemometrics

The conventional approach for determining analyte concentrations in Raman spectroscopy and in chemometrics generally is to apply some form of predictive model, e.g., a multiple linear regression, a principal components regression (PCA), or a "partial least squares" regression (PLS), in an attempt to best "predict" the known concentrations of the analyte(s) of interest in the samples. These techniques attempt to achieve the highest squared multiple correlations or the lowest sums-of-squares error from the observed spectral curves acquired from the samples. In this context, the individual bins in the spectral curves are considered to be the "independent" variables and the known analyte concentrations in the samples which are required by these methods are the "dependent" variables. The usual approach, therefore, is a "blind" procedure in which little or no knowledge is incorporated into the models regarding either the spectral features of the component analytes or how the signals generated by these analytes combine to give rise to the observed spectral curves.

The primary model employed in the current disclosure, which can be executed using the host computer or a different computing device with access to the Raman signal data, differs greatly from the above methods in that it fully incorporates domain knowledge regarding: (1) the spectral features of the underlying analytes obtained from any of measurements, the literature, or QM molecular modeling; (2) the ways in which the signals from these underlying or component analytes combine to produce the observed spectral curves acquired from the sample; and (3) how the spectral features are related to one another across both analytes and samples. In addition, when fitting the model, no use is made of known analyte concentrations for the samples (the "dependent variables" mentioned in the preceding paragraph). The incorporation of domain knowledge makes for a far more sensitive and stable model, as well as one that is far more immune to undesirable curve fitting.

The fundamental equation describing the model is:

$$S_{ji} = \Sigma_k W_{jk} A_{ki} + E_{ji} \quad (1)$$

in which $S_{ji}$ is the intensity of the signal observed for the j-th sample in the i-th spectral bin, $W_{jk}$ is the concentration of k-th component analyte in the j-th sample, $A_{ki}$ is the intensity of the signal in the i-th spectral bin for the k-th component analyte, and $E_{ji}$ is the error or residual for the j-th sample and i-th spectral bin.

Equation (1) can be expressed in matrix form as:

$$S = WA + E \quad (2)$$

To fit the model, a processor is configured to solve for matrices W and A such that the Frobenius norm (C), a measure of how well the model fits the data, is minimized subject to numerous constraints on W and A.

$$C=\|S-WA\|2 \quad (3)$$

Put another way, execution of the model optimally reproduces the observed spectral curves acquired from the samples by concentration-weighted sums of the spectral curves of pure or "component" analytes.

As can be seen, the model involves a type of matrix factorization and, possibly, dimensional reduction, not unlike that obtained from a singular value decomposition. In contrast to the matrix factorizations commonly employed in dimensional reduction schemes such as Principal Components, the disclosed factorization removes the requirement for orthogonality, which is replaced by numerous other constraints. The constraints incorporate domain knowledge regarding spectral features as well as the physics of the phenomena into the model.

More specifically, the constraints can include one or more of: A) non-negativity of the matrices S, A, and W due to the fact that the number of photons received in any spectral bin must be equal to or greater than zero and the concentration of any analyte in any sample must also be equal to or greater than zero; B) A-priori specification of a subset of the component analyte curves in A based on domain knowledge. These preset curves can be fixed based on known spectral curves (e.g., curves based on measurements, the literature, or QM molecular modelling) for a variety of analytes such a glucose, bilirubin, cholesterol, and hemoglobin, as well as variations thereof to account for context dependent shifts in spectral peaks. Partial specifications and "biases" may also be specified for some rows of A. This allows less precise or complete knowledge to be brought into the model by the use of "softer" or "fuzzier" constraints.

Factors upon which such partial specifications can be based include estimations based on examinations of the residuals from previously fitted models, knowledge of how certain spectral signals are associated with certain molecular bonds, and so on. Some rows of A may be left mostly unconstrained except for non-negativity, and perhaps sparseness; C) in addition, some "bias" may be applied to certain columns of W to improve the model in terms of its correlations with the dependent variables. These biases can be kept small to avoid the potential for undesirable curve fitting. It should be noted, however, that such biases will have no effect on those rows of A that contain fully-specified component analyte curves, and little effect on those rows that contain partially specified curves or features; the effect is largest on the mostly unconstrained rows of A; and D) there is no orthogonality constraint on any of the matrices involved as there is no reason to expect the spectral curves of various analytes to be orthogonal. In fact, it is known that different analytes can and often do have some overlapping spectral peaks which implies non-orthogonality. Likewise, the concentrations of analytes in the samples can generally be assumed to be non-orthogonal (with the exception of pure analytes in vials of one vial per analyte). Similarly, the spectral curves obtained from the samples are rarely orthogonal. For conventional dimensional reduction techniques using orthogonally-constrained models, for the underlying chemistry to be accurately represented, any orthogonal solution would need to be "rotated" to some more meaningful oblique solution. In the model disclosed herein, no such rotations are necessary. In terms of nomenclature, the disclosed model can be termed a "direct non-negative oblique procrustean factor model."

In a training or model building process, training data including inputs for matrices W and S are used to determine the analyte matrix A by solving equation (3). The training data can include the semi-synthetic data described above. Once matrix A is determined, the host computer can execute the model to determine analyte concentrations in new in vivo samples. This is done by solving for the concentration matrix W given S, which contains the sample's observed spectral curve, and analyte matrix A obtained during the training/model-building process. The algorithm used to determine W, given A, can include any good non-negative linear least-squares equation solver although other algorithms that allow additional constraints to be added can be used as well.

The quality of the model may be assessed by correlating, for each analyte in the training data, the concentrations found in W with the measured or known concentrations for the same set of samples (e.g., by comparison of glucose concentrations found in W with those obtained using a standard glucometer). Variations of the model described above can be implemented. However, it is noted that to obtain accurate analyte concentration measurement from Raman signals, a critical element is the explicit incorporation of substantial amounts of domain knowledge, and knowledge-based biases, into the model. Raman spectra of samples containing an unknown (and generally large) number of analytes present an extremely large set of independent variables that cannot be reduced beforehand by blind multivariate prediction or correlation-based models (including simple feed-forward neural networks) without severe curve-fitting and loss of information. Accordingly, such blind multivariate prediction or correlation-based models are not employed in the context of the present disclosure. However, neural networks and other machine learning methods can also be employed to detect and correct outliers, as well as improve the overall accuracy of the measurements, in the context of a model such as that described herein.

It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components and/or steps described and illustrated with reference to the figures are required for all embodiments or arrangements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having,"

"containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the disclosure as understood by a person having ordinary skill in the art.

What is claimed is:

1. A probe for non-invasively interrogating an in vivo sample for measurement of analytes comprising:
    a laser generator for outputting a laser radiation having a wavelength, power and diameter;
    a scanning mirror positioned to receive the laser radiation; and
    a mechanical driver coupled to the scanning mirror and adapted to move the scanning mirror such that the scanning mirror moves a focal spot of the laser radiation over an area of the sample over time, thus providing a reduction in average radiation intensity at any given point on or in the sample;
    collection optics, positioned to track the focal point of the laser on the sample, and to receive Raman signals and Rayleigh scattered laser radiation elicited by impact of the laser radiation at the focal spot on the sample, and emanating therefrom, via the same scanning mirror;
    a window bearing a central mirror positioned between the laser generator and scanning mirror, the central mirror positioned to redirect laser radiation transmitted from the laser generator along a first optical path to the scanning mirror, and the window allowing Raman signals and Rayleigh scattered laser radiation to pass along a second optical path toward a detector; and
    a long-pass filter designed to block at least 99.999 percent of the Rayleigh-scattered radiation at the wavelength of the laser radiation and to pass the Raman signals along the second optical path;
    wherein the Raman signals that emanate from the sample contain data from which the analytes in the same can be determined.

2. The probe of claim 1 wherein the mechanical driver comprises a motor and a shaft, the shaft is coupled to and adapted to cause the scanning mirror to rotate.

3. The probe of claim 1, wherein the mechanical driver comprises a piezoelectric element that is coupled to the scanning mirror and adapted to move the mirror.

4. The probe of claim 1, wherein the radiation intensity impacting the sample is less than 1 W/cm$^2$.

5. A method for non-invasively interrogating an in vivo sample for measurement of analytes comprising:
    generating laser radiation having a wavelength, power and diameter; and
    deflecting the laser radiation onto the sample such that a focal point of the laser radiation scans over an area of the sample over time resulting in a reduced average radiation intensity on the sample at any single location;
    collecting Raman signals elicited from the impact of the laser radiation at the focal point on the sample and emanating therefrom, wherein the Raman signals that emanate from the sample contain data from which the analytes in the same can be determined;
    redirecting radiation scattered from the sample along a second path, also including the scanning component, toward a detector; and
    filtering out the at least 99.999 percent of Rayleigh-scattered radiation at a wavelength of the laser radiation.

6. The method of claim 5 wherein the radiation is deflected by a rotating mirror adapted to deflect radiation onto the sample such that such that the deflected radiation traces a pattern on the sample surface.

7. The method of claim 5, wherein the radiation intensity impacting the sample is less than 1 W/cm$^2$.

8. A system for non-invasively interrogating an in vivo sample for measurement of analytes comprising:
    a pulse sensor coupled to the in vivo sample adapted to detect a blood pulse of the sample and to generate a corresponding pulse signal;
    a laser generator for outputting laser radiation having a wavelength, power and an original diameter, the laser radiation being directed toward the sample and adapted to elicit Raman signals from the sample;
    a laser controller adapted to turn the laser generator on and off;
    a spectrometer situated to receive the Raman signals and to generate spectral data from which analyte concentrations can be computed; and
    a computing device coupled to the pulse sensor, laser controller and spectrometer, the computing device adapted to correlate the spectral data with the pulse signal received from the pulse sensor based on timing data received from the laser controller in order to isolate spectral components from analytes within the blood of the sample from spectral components from analytes arising from non-blood components of the sample.

9. The system of claim 8, wherein the computing device is configured to compute an exponential moving average of the pulse signal and to send a signal to the laser controller for activating the laser generator, in a first pass, when the pulse signal obtained from the pulse sensor falls below the exponential moving average of the pulse signal, and in a second pass activating the laser generator when the pulse signal rises above the exponential moving average of the pulse signal.

10. The system of claim 8, wherein the computing device computes a difference between spectral data received during the first pass and spectral data received during the second pass.

11. The system of claim 8, further comprising a scanning mirror adapted to deflect the laser radiation onto the sample such that a surface area on the sample that the laser radiation impacts is greater than the original beam diameter with a corresponding drop in radiation intensity at any location on the sample surface.

12. The system of claim 8, wherein the wavelength of the laser radiation produced by the laser generator is selected to elicit resonant enhancement of at least one analyte of interest contained within the sample.

13. A method for non-invasively interrogating an in vivo sample for measurement of analytes comprising:
    detecting a pulse signal of blood of the in vivo sample;
    generating laser radiation having a wavelength, power and an original diameter at controllable times, the laser radiation being directed toward the sample to elicit Raman signals from the sample;

deriving analyte spectral data from the Raman signals; and correlating the spectral data with the pulse signal and timing of laser generation so as to isolate spectral components from analytes within the blood of the sample from spectral components from analytes arising from non-blood components of the sample.

14. The method of claim 13, further comprising:

computing an exponential moving average of the pulse signal; and controlling the laser generator to, during a first pass, turn on the laser generator when the pulse signal falls below the exponential moving average of the pulse signal, and during a second pass, turn on the laser generator when the pulse signal rises above the exponential moving average of the pulse signal, wherein spectral data is derived only during peaks and valleys of the blood pulses.

15. The method of claim 14, further comprising:

computing a difference between the spectral data generated during the peaks of the blood pulses from the spectral data generated during the valleys of the blood pulses in order to isolate blood analytes.

16. The method of claim 14, further comprising deflecting the laser radiation onto the sample such that a surface area on the sample impacted by the laser radiation is greater than the original diameter and radiation intensity at any location on the sample is reduced.

17. A method for non-invasively interrogating an in vivo sample for measurement of analytes comprising:

providing a first laser radiation of a first wavelength and a second laser radiation of a second wavelength;

detecting a pulse signal of blood of the in vivo sample;

during a single exposure, alternately switching on the laser radiation of the first and second wavelengths when the pulse signal either falls below or rises above the exponential moving average of the pulse signal so that radiation of only one wavelength is directed to the sample at a time to elicit Raman signals from the sample;

wherein spectral data is generated only during peaks and valleys of the blood pulses, producing superimposed, added and shifted first and second analyte spectral data from the Raman signals generated by impact of the first and second laser radiation on the sample; and separating, using a mathematical model, the superimposed, added, and shifted first and second analyte spectral data to remove effects of background radiation and to isolate a signal from the blood.

18. The method of claim 17, wherein the wavelength of the second laser radiation is shifted from the wavelength of the first laser radiation by two nanometers or less.

19. A probe for non-invasively interrogating an in vivo sample for measurement of analytes comprising:

a laser generator for outputting a laser radiation having a wavelength, power and diameter;

a scanning mirror positioned to receive the laser radiation; and a mechanical driver coupled to the scanning mirror and adapted to move the scanning mirror such that the scanning mirror moves a focal spot of the laser radiation over an area of the sample over time, thus providing a reduction in average radiation intensity at any given point on or in the sample;

collection optics, positioned to track the focal point of the laser on the sample, and to receive Raman signals and Rayleigh scattered laser radiation elicited by impact of the laser radiation at the focal spot on the sample, and emanating therefrom, via the scanning mirror;

a window bearing a central mirror positioned between the laser generator and scanning device, the central mirror positioned to redirect laser radiation transmitted from the laser generator along a first optical path to the scanning mirror, and the window allowing Raman signals and Rayleigh scattered laser radiation to pass along a second optical path toward a detector;

a long-pass filter designed to block at least 99.999 percent of the Rayleigh-scattered radiation at the wavelength of the laser radiation and to pass the Raman signals along the second optical path;

a condenser lens positioned further along the second optical path toward the detector and adapted to focus the Raman signals and remaining laser radiation received through the long-pass filter; and a fiber positioned to receive the Raman signals focused by the condenser lens and adapted to deliver the Raman signals and remaining laser radiation to the detector, wherein the Raman signals that emanate from the sample contain data from which the analytes in the same can be determined.

* * * * *